US010837050B2

(12) United States Patent
Vogelstein et al.

(10) Patent No.: US 10,837,050 B2
(45) Date of Patent: Nov. 17, 2020

(54) METHODS FOR BEAMING

(71) Applicant: The Johns Hopkins University, Baltimore, MD (US)

(72) Inventors: Bert Vogelstein, Baltimore, MD (US); Frank Diehl, Baltimore, MD (US); Kenneth W. Kinzler, Baltimore, MD (US); Meng Li, San Francisco, CA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/184,338

(22) Filed: Nov. 8, 2018

(65) Prior Publication Data
US 2020/0123600 A1 Apr. 23, 2020

Related U.S. Application Data

(63) Continuation of application No. 15/174,427, filed on Jun. 6, 2016, now Pat. No. 10,150,991, which is a continuation of application No. 12/091,395, filed as application No. PCT/US2006/041115 on Oct. 20, 2006, now Pat. No. 9,360,526.

(60) Provisional application No. 60/729,235, filed on Oct. 24, 2005.

(51) Int. Cl.
*C12Q 1/6858* (2018.01)
*H02H 1/00* (2006.01)
*H02H 3/33* (2006.01)
*G01R 31/50* (2020.01)
*G01R 31/327* (2006.01)

(52) U.S. Cl.
CPC ....... *C12Q 1/6858* (2013.01); *G01R 31/3277* (2013.01); *G01R 31/50* (2020.01); *H02H 1/0015* (2013.01); *H02H 3/33* (2013.01)

(58) Field of Classification Search
None
See application file for complete search history.

(56) References Cited

U.S. PATENT DOCUMENTS

| | | | |
|---|---|---|---|
| 5,888,778 A | 3/1999 | Shuber | |
| 6,355,431 B1 | 3/2002 | Chee et al. | |
| 8,048,627 B2 | 11/2011 | Dressman et al. | |
| 9,360,526 B2 * | 6/2016 | Vogelstein | ............ A61P 9/10 |
| 10,150,991 B2 * | 12/2018 | Vogelstein | ........... C12Q 1/6858 |
| 2002/0086808 A1 | 7/2002 | Nyssen et al. | |
| 2002/0119459 A1 | 8/2002 | Griffiths | |
| 2005/0079510 A1 | 4/2005 | Berka et al. | |
| 2005/0227264 A1 | 10/2005 | Nobile et al. | |
| 2006/0019274 A1 | 1/2006 | Goel | |
| 2006/0228721 A1* | 10/2006 | Leamon | ........... C12Q 2565/301 435/6.14 |
| 2007/0065823 A1 | 3/2007 | Dressman et al. | |
| 2008/0242560 A1 | 10/2008 | Gunderson | |

FOREIGN PATENT DOCUMENTS

| WO | 3106678 | 12/2003 |
|---|---|---|
| WO | 2004069849 | 8/2004 |
| WO | 2007050465 | 5/2007 |

OTHER PUBLICATIONS

Ahlquist, D. A. et al., "Stool screening for colorectal cancer: evolution from occult blood to molecular markers." Clin Chim Acta., Jan. 2002 , 315(1-2):157-68.
Andre P at el., "Fidelity and mutational spectrum of Pfu DNA polymerase on a human mitochondrial DNA sequence." Genome Res., Aug. 1997, 7(8):843-52.
Bernath, K., et al., "In vitro compartmentalization by double emulsions: sorting and gene enrichment by fluorescence activated cell sorting." Anal Biochem, Feb. 1, 2004, 325(1), 151-7.
Breen, et al., "Toward a system of cancer screening in the United States: trends and opportunities." Annu Rev Public Health, 2005, 26:561-82.
Bremnes, et al., "Circulating tumour-derived DNA and RNA markers in blood: a tool for early detection, diagnostics, and follow-up?" Lung Cancer., Jul. 2005, 49(1):1-12.
Brisco et al., "Detection and Quantitation of Neoplastic Cells in Acute Lymphoblastic Leukaemia, by Use of the Polymerase Chain Reaction," British Journal of Haematology, 1991, 79, 211-217.
Brisco et al., "Outcome Prediction in Childhood Acute Lymphoblastic Leukaemia by Molecular Quantification of Residual Disease at the End of Induction," The Lancet, Jan. 22, 1994, vol. 343, pp. 196-200.
Burchill, et al., "Molecular detection of low-level disease in patients with cancer." J Pathol, Jan. 2000, 190(1):6-14.
Cerar et al., "Colorectal carcinoma in endoscopic biopsies; additional histologic criteria for the diagnosis," Pathol Res Pract 2004, 200(10):657-62.
Chen et al., "Pivotal study of iodine-131-labeled chimeric tumor necrosis treatment radioimmunotherapy in patients with advanced lung cancer," J Clin Oncol, Mar. 1, 2005, 23(7):1538-47.
Choi et al., "The role of macrophages in the in vitro generation of extracellular DNA from apoptotic and necrotic cells," Immunology, May 2005, 115(1):55-62.

(Continued)

*Primary Examiner* — Young J Kim
(74) *Attorney, Agent, or Firm* — Fish & Richardson P.C.

(57) ABSTRACT

Improvements on the basic method used for BEAMing increase sensitivity and increase the signal-to-noise ratio. The improvements have permitted the determination of intrinsic error rates of various DNA polymerases and have permitted the detection of rare and subtle mutations in DNA isolated from plasma of cancer patients.

11 Claims, 14 Drawing Sheets

Specification includes a Sequence Listing.

(56) References Cited

OTHER PUBLICATIONS

Celine et al., "PCR fidelity of Pfu DNA polymerase and other thermostable DNA polymerases," Nucleic Acids Research (1996) 24(18): pp. 3546-3551.
Diehl et al., "Detection and Quantification of Mutations in the Plasma of Patients with Colorectal Tumors," Proceedings of the National Academy of Sciences, Nov. 8, 2005, vol. 102, No. 45, pp. 16368-16373.
Ding et al., "MS analysis of single-nucleotide differences in circulating nucleic acids: Application to noninvasive prenatal diagnosis," Proceedings of the National Academy of Sciences, USA (2004) 101 (29): pp. 10762-10767.
Dressman et al., "Transforming Single DNA Molecules into Fluorescent Magnetic Particles for Detection and Enumeration of Genetic Variations," Proc. Natl. Acad. Sci, 2003 vol. 100, No. 15, pp. 8817-8822.
Extended European Search Report dated Jan. 24, 2012, in corresponding Application No. 11191989.
Extended European Search Report dated Oct. 7, 2009, in corresponding Application No. 06817236.0.
Fan et al., "Parallel Genotyping of Human SN P's Using Generic High-Density Oligonucleotide Tag Arrays," Genome Research, Jun. 2000, vol. 10 No. 6, pp. 853-860.
Ghadessy et al., "A novel emulsion mixture for in vitro compartmentalization of transcription and translation in the rabbit reticulocyte system," Protein Eng Des Sel., Mar. 1 2004, 17(3):201-4.
Giacona et al., "Cell-free DNA in human blood plasma: length measurements in patients with pancreatic cancer and healthy controls," Pancreas, Jul. 1998, 17(1):89-97.
Goessl, C. "Diagnostic potential of circulating nucleic acids for oncology," Expert Rev Mol Diagn, Jul. 2003, 3(4):431-42.
Hardenbol at el., "Multiplexed genotyping with sequence-tagged molecular inversion probes," Nat. Biotechnol., Jun. 2003, 21(6):673-8.
Hatch et al., "Rolling circle amplification of DNA immobilized on solid surfaces and its application to multiplex mutation detection," Genetic Analysis: Biomolecular Engineering (1999) 15(2): pp. 35-40.
International Search Report for PCT/US2006/041115, dated Aug. 31, 2007, 2 pages.
International Preliminary Report on Patentability for PCT/US2006/041115, dated Apr. 29, 2008, 7 Pages.
Jaffer et al., "Molecular imaging in the clinical arena," Jama, Feb. 16, 2005, 293(7):855-62.
Jahr et al., "DNA fragments in the blood plasma of cancer patients: quantitations and evidence for their origin from apoptotic and necrotic cells," Feb. 15, 2001, 61(4):1659-65.
Kaplan, R. M., "Screening for cancer: are resources being used wisely?" Recent Results Cancer Res, 2005, 166:315-34.
Keohavong et al., "Fidelity of DNA Polymerases in DNA Amplification," Proc. Natl.Acad. Sci, 1989, vol. 86, pp. 9253-9257.
Khrapko, et al. "Mitochondrial mutational spectra in human cells and tissues," Proc. Natl. Acad. Sci. 94, Dec. 9, 1997, 94(25):13798-803.
Kinzler et al., "Lessons from hereditary colorectal cancer," Cell, Oct. 18, 1996, 87(2):159-70.
Larsson C et al. "In situ genotyping individual DNA molecules by target-primed rolling-circle amplification of padlock probes," Nature Meth, Dec. 2004, 1(3):227-32.
Leek et al., "Necrosis correlates with high vascular density and focal macrophage infiltration in invasive carcinoma of the breast," Br J Cancer, Feb. 1999, 79(5-6):991-5.
Leon et al., "Free DNA in the serum of cancer patients and the effect of therapy," Cancer Res., Mar. 1977, 37(3):646-50.
Li et al., "Beaming up for Detection and Quantification of Rare Sequence Variants," Nature Methods, Feb. 2006, vol. 3 No. 2, pp. 95-97, + 4 pages of Supplementary Methods.

Lieberman et al., "Review article: balancing the ideal versus the practical-considerations of colorectal cancer prevention and screening," Aliment Pharmacol Ther., Feb. 2004, 19 Suppl 1:71-6.
Lizardi et al., "Mutation detection and single-molecule counting using isothermal rolling-circle amplification," Nature Genetics (1998) 19: pp. 225-232.
Lo et al., "Rapid clearance of fetal DNA from maternal plasma," Am J Hum Genet, Jan. 1999, 64(1): 218-224.
Lotze et al., "Workshop on cancer biometrics: identifying biomarkers and surrogates of cancer in patients: a meeting held at the Masur Auditorium, National Institutes of Health," J Immunother., Mar.-Apr. 2005, 28(2):79-119.
Margulies M et al., "Genome sequencing in microfabricated high-density picolitre reactors," Nature., Sep. 15, 2005, 437(7057):376-80.
Mccalla et al., "Steric Effects and Mass-Transfer Limitations Surrounding Amplification Reactions on Immobilized Long and Clinically Relevant DNA Templates," Langmuir Article, American Chemical Society (2009) 25(11 ): pp. 6168-6175.
Meyerhardt et al., "Systemic Therapy for Colorectal Cancer," Feb. 3, 2005, 352(5):476-87.
Muller et al., "Methylated DNA as a possible screening marker for neoplastic disease in several body fluids," Expert Rev Mol Diagn., Jul. 2003, 3(4):443-58.
Muniappan et al., "The DNA polymerase beta replication error spectrum in the adenomatous polyposis coli gene contains human colon tumor mutational hotspots," Cancer Res., Jun. 1 2002, 62(11):3271-5.
Nakano et al., "Single-Molecule PCR Using Water-In-Oil Emulsion," J. Biotechnology, 2003, vol. 102, pp. 117-124.
Nallur et al., "Signal amplification by rolling circle amplification on DNA microarrays," Nucleic Acids Research (2001) 29(23): e118, pp. 1-9.
Nilsson et al., "Padlock probes: circularizing oligonucleotides for localized DNA detection," Science., Sep. 30, 1994, 265(5181):2085-8.
Qi et al., L-RCA (ligation-rolling circle amplification): a general method for genotyping of single nucleotide polymorphisms (SNPs), Nucleic Acids Research (2001) 29(22): e116, pp. 1-7.
Ransohoff, Df., "Bias as a threat to the validity of cancer molecular-marker research," Nat Rev Cancer., Feb. 2005, 5(2):142-9.
Shendure et al., "Accurate Multiplex Polony Sequencing of an Evolved Bacterial Genome," Science, Sep. 9, 2005, vol. 309, pp. 1-6 + 41 pages of Supporting Online Material.
Sidransky et al., "Identification of p53 gene mutations in bladder cancers and urine samples," Science., May 3, 1991, 252(5006):706-9.
Sidransky et al., "Identification of ras oncogene mutations in the stool of patients with curable colorectal tumors," Science, Apr. 3, 1992, 256(5053):102-5.
Sidransky, D., "Emerging molecular markers of cancer," Nat. Rev. Cancer, Mar. 2002, 2(3):210-9.
Smith et al., "American Cancer Society Guidelines for the Early Detection of Cancer, 2005," CA Cancer J Clin., Jan.-Feb. 2005, 55(1):31-44.
Sozzi et al., "Analysis of circulating tumor DNA in plasma at diagnosis and during follow-up of lung cancer patients.," Cancer Res., Jun. 15, 2001, 61(12):4675-8.
Sykes et al., "Quantitation of Targets for PCR by Use of Limiting Dilution," Bio Techniques, 1992, vol. 13, No. 3, pp. 444-449.
Thomas et al., "Amplification of Padloc Probes for DNA Probes for DNA Diagnostics by Cascade Rolling Circle Amplification or the Polymerase Chain Reaction," Arch. Pathol Lab. med., Dec. 1999, vol. 123 pp. 1170-1176.
Thomlinson et al., "The histological structure of some human lung cancers and the possible implications for radiotherapy," Br. J. Cancer., Dec. 1955, 9(4): 539-549.
Tiemann-Boege et al., "Product Length, Dye Choice, and Detection Chemistry in the Bead-Emulsion Amplification of Millions of Single DNA Molecules in Parallel," Analytical Chemistry (2009) 81 (14): pp. 5770-5776.
Valentine et al., "Mutagenesis by Peroxy Radical Is Dominated by Transversions at Deoxyguanosine: Evidence for the Lack of Involvement of 8—0xo-dG' and/or Abasic Site Formation," Biochemistry (1998) 37(19): pp. 7030-7038.

(56) References Cited

OTHER PUBLICATIONS

Vogelstein et al., "Cancer genes and the pathways they control," Nat. Med., Aug. 2004, 10,(8):789-99.

Wang et al., "Rapid and Sensitive Detection of Severe Respiratory Syndrome Coronavirus by Rolling Circle Amplification," Journal of Clinical Microbiology (2005) 43(5): pp. 2339-2344.

Winawer et al., "Workgroup II: the screening process. UICC International Workshop on Facilitating Screening for Colorectal Cancer, Oslo, Norway (Jun. 29-30, 2002)," Ann. Oncol., Jan. 2005, 16(1):31-33.

Written Opinion of the Internatioal Search Authority for PCT/US2006/41115, dated Aug. 31, 2007, 5 pages.

Yu et al., "Tissue disposition of 2'-O-(2-methoxy) ethyl modified antisense oligonucleotides in monkeys," J. Pharm Sci., Jan. 2004, 93(1):48-59.

\* cited by examiner

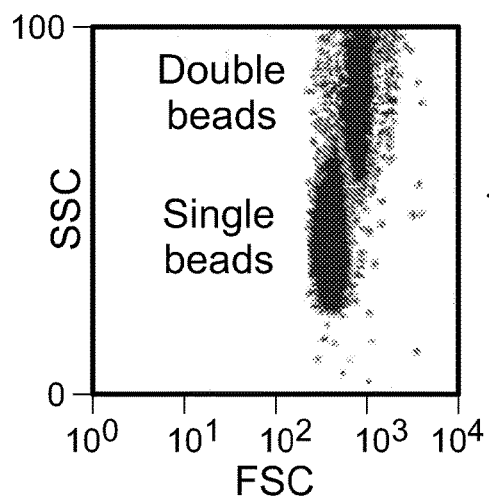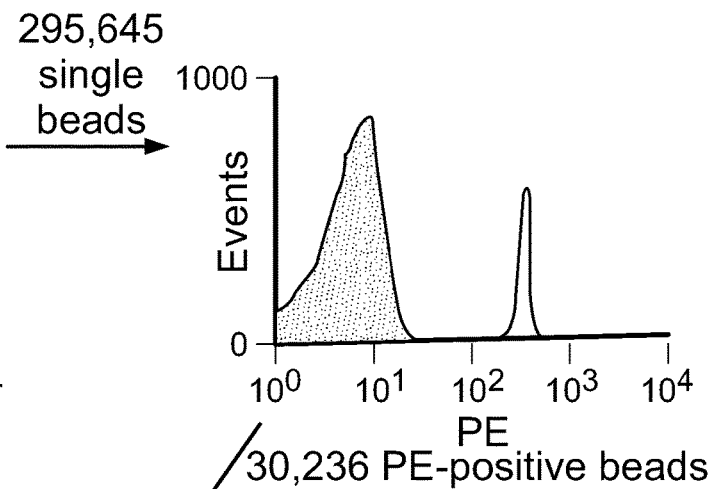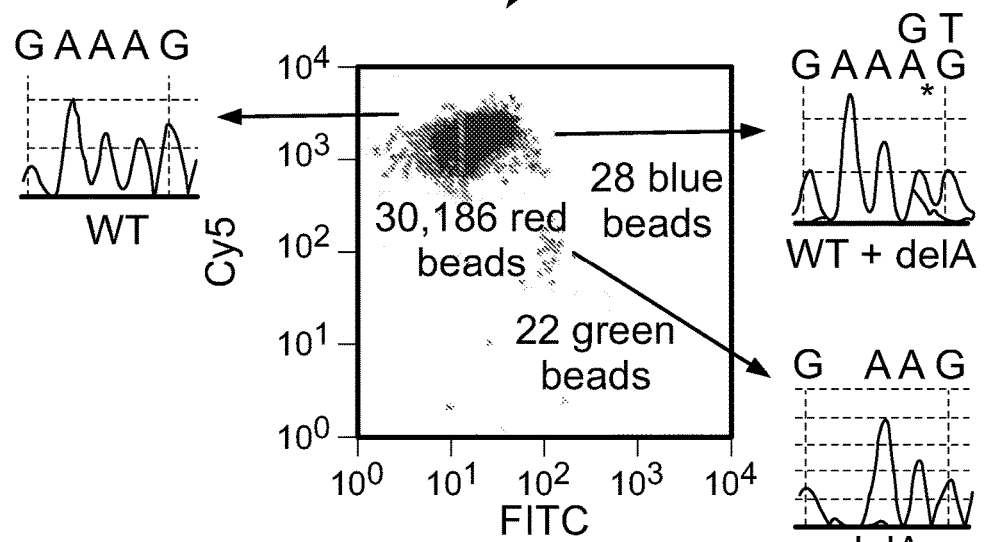
FIG. 3A
FIG. 3B
FIG. 3C

1

METHODS FOR BEAMING

CROSS-REFERENCE TO RELATED APPLICATIONS

This application is a continuation application of and claims priority to U.S. application Ser. No. 15/174,427, filed on Jun. 6, 2016, now U.S. Pat. No. 10,150,991, which is a continuation application of and claims priority to U.S. application Ser. No. 12/091,395, filed on Nov. 24, 2010, now U.S. Pat. No. 9,360,526, which is a National Stage Application under 35 U.S.C. § 371 and claims the benefit of International Application No. PCT/US2006/041115, filed on Oct. 20, 2006, which claims priority to U.S. Provisional Application No. 60/729,235, filed on Oct. 24, 2005. The entire contents of the foregoing are incorporated herein by reference.

TECHNICAL FIELD OF THE INVENTION

This invention is related to the area of analytical biochemistry and diagnostics. In particular, it relates to detecting subtle and rare differences in nucleic acid molecules.

BACKGROUND OF THE INVENTION

The probability of curing cancers, through surgery alone, is high in those individuals whose primary tumors are detected at a relatively early stage. Such early detection is therefore one of the most promising approaches for limiting cancer morbidity and mortality in the future (1). At present, PAP smears can be used to detect cervical cancers, mammography can detect breast cancers, serum PSA levels can signify the presence of prostate cancer, and colonoscopy and fecal occult blood tests can detect colon cancers (2). However, problems in sensitivity, specificity, cost or compliance have complicated widespread implementation of these tests (3-5). Moreover, methods for the early detection of most other cancer types are not yet available.

The discovery of the genetic bases of neoplasia has led to new approaches to detect tumors non-invasively (6-8). Many of these approaches rely on the ex vivo detection of mutant forms of the oncogenes and tumor suppressor genes that are responsible for the initiation and progression of tumors. This approach was first used to detect bladder and colon tumors through examination of urine and stool, respectively (9, 10), and has since been used to detect several other tumor types (11-14). As the mutant genes are not only "markers" for cancer, but are the proximate causes of tumor growth (1), they have major conceptual advantages over conventional markers such as fecal occult blood or serum PSA. In particular, conventional markers are not pathogenically involved in the tumorigenic process and are much less specific for neoplasia than are mutations.

The evaluation of patient blood samples for mutant DNA molecules is a particularly attractive approach as such tests could detect many different forms of cancers. Additionally, blood can be easily obtained from patients during routine outpatient visits and methods for preparing and storing plasma and serum are well-known and reliable. Accordingly, numerous studies have attempted to identify abnormal forms or quantities of DNA in plasma or serum (6, 11-15). Unfortunately, the results of many of these studies are contradictory. Some report high detection rates of cancers, others very low, despite the use of similar techniques and patient cohorts. Moreover, several studies have shown that loss of heterozygosity is routinely detectable in circulating DNA, even in patients with relatively non-aggressive tumors. To detect loss of heterozygosity in such samples, the neoplastic cells within a tumor must contribute more than 50% of the total circulating DNA.

The prior studies, though promising, lead to several questions that must be answered to engender confidence in the use of circulating, abnormal DNA as a biomarker of malignancy. First, how many copies of a given gene fragment are present in the circulation in cancer patients? Second, what is the nature of this DNA, e.g., intact vs. degraded? Third, what fraction of these gene fragments have an abnormal (e.g., mutant) DNA sequence? And fourth, how does this fraction vary with stage of disease? To answer these questions, it is necessary to develop technologies that can simultaneously quantify the number of normal and mutant DNA molecules in a given sample, even when the fraction of mutant molecules is very small. Such sensitive and accurate assays for the detection and quantification of rare variants among a large excess of normal sequences have important applications in many areas of biomedical research. Examples in basic scientific research include the analysis of replication fidelity in various in vitro systems and the determination of mutation rates in cells after treatment with mutagens. Examples in clinical medicine include the identification of mutations in the blood, urine, or stool of cancer patients and the identification of fetal DNA sequences in the plasma of pregnant women.

We previously described an approach, called BEAMing (beads, emulsions, amplification, and magnets), which allows the transformation of a population of DNA fragments into a population of beads each containing thousands of copies of the identical sequence. The bead population generated in this fashion has been shown to accurately represent the initial DNA population. Because $10^8$ beads can be generated in a single test tube and analyzed by standard flow cytometry, this technique has the capacity not only to identify genetic variations present in the original DNA population, but also to quantify precisely their number in comparison to wild-type sequences. In addition to their use for discovering such rare variants, beads generated through the BEAMing process provide excellent templates for nucleotide sequencing, for example, sequencing-by-synthesis. The beads can also be used as templates for both the high-throughput methods recently described for this purpose.

The advantages of having as many copies as possible per bead for both flow cytometric and sequencing applications are clear. We estimate that the number of copies per 1-micron bead produced by BEAMing is $10^4$-$10^5$. There is a need in the art for a technique that can increase this number by at least two orders of magnitude.

SUMMARY OF THE INVENTION

One embodiment of the invention provides a method for analyzing nucleotide sequence variations. A region of analyte DNA molecules is amplified using a high fidelity DNA polymerase to form a set of first amplicons. Microemulsions comprising said first amplicons and reagent beads are formed. The reagent beads are bound to a plurality of molecules of a primer for amplifying the set of first amplicons. The first amplicons are amplified in the microemulsions. Product beads are thereby formed which are bound to a plurality of copies of second amplicons. A sequence feature of the second amplicons is determined by single base extension of a primer bound to the second amplicons using at least two differentially labeled dideoxyribonucleotides.

A second embodiment of the invention provides a method for amplifying a region of analyte DNA molecules. A region of analyte DNA molecules is amplified using a high fidelity DNA polymerase to form a set of first amplicons. Microemulsions comprising said first amplicons and reagent beads are formed. The reagent beads are bound to a plurality of molecules of a primer for amplifying the set of first amplicons. The first amplicons are amplified in the microemulsions. Product beads are formed which are bound to a plurality of copies of second amplicons. The microemulsions are broken. The second amplicons are amplified using rolling circle amplification to form third amplicons.

These and other embodiments which will be apparent to those of skill in the art upon reading the specification provide the art with methods for analysis, diagnosis, and screening of subtle and rare nucleic acid differences and the conditions or agents which cause such differences.

BRIEF DESCRIPTION OF THE DRAWINGS

FIG. 1A. The concentration of total APC fragments (wild-type plus mutant) of various sizes was determined using digital PCR of plasma DNA from three different patients (patients 29, 30 and 32). FIG. 1B. The fraction of mutant APC fragments was determined by digital sequencing of PCR products.

FIG. 2A. Extended beads were prepared by modifications of the BEAMing procedure described in Dressman et al (16) FIG. 2B. Single base extensions were performed on the extended beads (gold spheres). Normal DNA sequences contained a G at the queried position, while mutant sequences contained an A.

FIGS. 3A-3C. Processing of flow cytometry data obtained by BEAMing. FIG. 3A. Dot plot of forward scatter (FCS) and side scatter (SCC) signals of beads. FIG. 3B. Histogram of single beads with regards to PE signal. Only beads containing extended PCR products had PE signals, as depicted in FIG. 2B. FIG. 3C. Dot plot showing the Cy5 and FITC fluorescence intensity profiles of PE-positive beads. The beads clustered in three distinct populations colored red, green, and blue. Sequencing of individual beads sorted from each population showed that the red and green beads contained homogeneous wild-type and mutant sequences, respectively, while the blue beads contained a mixture of wild-type and mutant sequences.

FIG. 8A. Examples of flow cytometric profiles. Cy5-labeled KRAS probes and FAM-labeled PIK3CA probes were hybridized to the beads. FIG. 8B. Relationship between input template ratio and bead proportions generated in PIK3CA and KRAS mixture. (n=2; Slope=1.0; R2=0.9999). FIG. 8C. Relationship between input template ratio and bead proportions generated in Tp53 and PIK3CA mixture (n=2; Slope=1.0; R2=0.9988).

FIG. 9A. P53 sequence specific FAM probes were hybridized to detect DNA bound to magnetic beads (100× magnifications) after different incubation times FIG. 9B. Relative Fluorescent intensity of FAM probes hybridized to the beads after RCA.

FIG. 10A. Example of flow cytometric profiles for quantification of TP53 codon 273 mutations in a series of dilutions. FIG. 10B. Relationship between input mutation ratio and mutant bead proportions generated in TP53 (n=8; slope=1.0; R2=0.9998). FIG. 10C. Example of flow cytometric data for quantification of PIK3CA A3140G mutation in a series of dilutions. FIG. 10D. Relationship between input mutation ratio and mutant bead proportions generated in PIK3CA (n=8; slope=1.0; R2=0.9998). FIG. 10E. Statistic linear relationship between input mutation ratio and mutant bead proportions generated in kras2. (n=8; slope=1.1; R2=0.999).

FIG. 11A. Example of flow cytometric profiles of PIK3CA exon 20 A3140G. FIG. 11B. Comparison of error rate of different polymerases per cycle at PIK3CA exon 20 A3140 G (n=8-16). FIG. 11C. Comparison of the error rate of different polymerases per cycle at TP53 exon 8 G818A (n=8-16).

TABLES

Figure 1A:
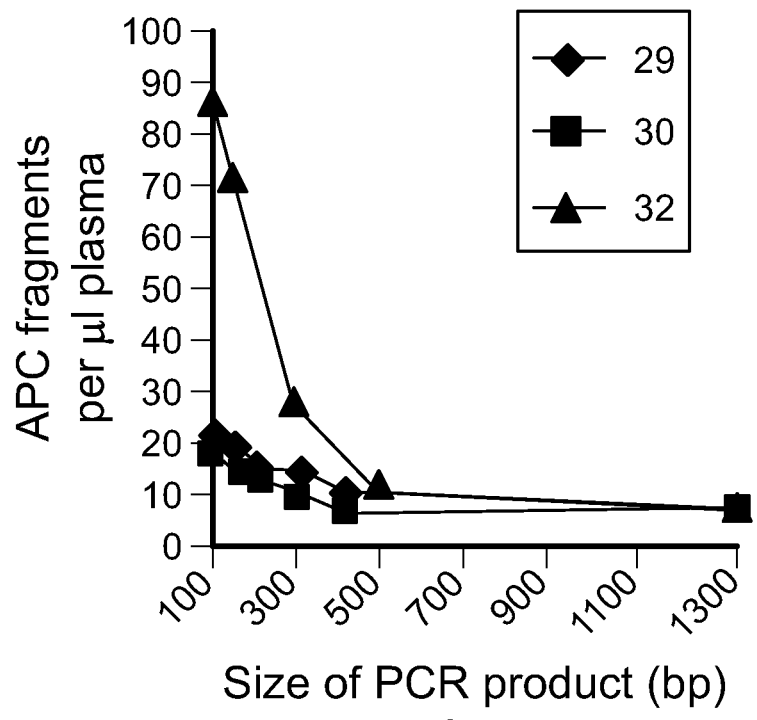
FIGS. 1A-1B. Effect of the PCR amplicon size on plasma DNA concentration and mutation frequency.

Table 1. Primer sequences used for fragment sizing
Table 2. Primer sequences used for BEAMing
Table 3. Primer sequences used for single base extension
Table 4. Quantification of APC gene mutations in plasma.
Table 5: Mutant genomic sequences analyzed
Table 6: Primers used for analysis of Tp53
Table 7: Primers used for analysis of PIK3CA
Table 8: Primers used for analysis of KRAS2

DETAILED DESCRIPTION OF THE INVENTION

The inventors have developed methods which improve the sensitivity of assays for rare and subtle nucleic acid differences. The assays are called BEAMing assays, and involve amplification of nucleic acid molecules on beads in microemulsions. One improvement involves the use of a high fidelity DNA polymerase in a preparatory amplification reaction. Another improvement involves the use of a single base extension reaction to determine a sequence feature on an amplified product of BEAMing. Another improvement involves the use of a rolling circle amplification to amplify the nucleic acids bound to beads as a result of BEAMing. Another improvement involves the use of a single base extension reaction to determine a sequence feature on an amplified product of BEAMing which has been further amplified using a rolling circle (isothermal) amplification. These improvements which can be used singly or in combinations provide increased sensitivity and/or signal-to-noise ratios.

High fidelity DNA polymerases which can be used are those which provide a higher rate of fidelity (lower rate of errors) than Taq polymerase. Preferably these provide an error rate of less than $10^{-5}$, more preferably an error rate of less than $5 \times 10^{-6}$, and even more preferably an error rate of less than $10^{-6}$. Suitable polymerases include: Phusion™ DNA polymerase (NEB), Taq High Fidelity™, and PfuUltra™. These are used in a thermal cycling polymerase chain reaction, as is conventional in the art.

Microemulsions are formed with beads and primers as previously taught. Because BEAMing requires thermal cycling, an emulsifier which is thermostable can be used. One such emulsifier is Abil® EM90 (Degussa—Goldschmidt Chemical, Hopewell, Va.). Other such emulsifiers can be used as are known in the art.

Amplicons can be any size which is efficiently amplified using polymerase chain reaction. In the case of templates obtained from serum of cancer patients, amplicons are preferably shorter than or equal to 300 bp, or shorter than or equal to 200 bp, or shorter than or equal to 100 bp. Templates from serum of colon cancer patients are apparently degraded to small sizes. Thus amplification of a smaller amplicon results in a more efficient and sensitive detection. The dependence of detection on size is quite strong as shown in FIG. 1.

Single base extension reaction with differentially labeled dideoxynucleotides provides a sensitive means for detecting sequence features. If upon detection of products, individual beads are found with multiple, distinct labels, for example, representing a mutant and a wild type nucleotide, they can be discarded from further analysis. Multiple, distinct labels in this context indicates that a bead was present in a microemulsion with two distinct templates of analyte DNA, rather than the desired single template, or that an error occurred early in an amplification reaction in a microemulsion, such that the erroneous and the correct templates were both amplified.

One means for detecting a sequence feature on an amplicon bound to a bead employs a single base extension (SBE) reaction. This reaction typically employs labeled dideoxynucleotide triphosphates to ensure that only a single monomer addition occurs. Dideoxynucleotide triphosphates can be conveniently labeled with any type of detectable label, including radioactive, fluorescent, and luminescent moieties. Different labels can be attached to different dideoxynucleotide triphosphates (ddNTPs) so that different products can be detected in the same sample. Prior to addition of all reagents necessary for initiation of the SBE reaction, unlabeled ddNTPs can be added to block non-specific extension. Typically at least one unlabeled ddNTP is added at a concentration five to 40 fold higher than the concentration of the labeled ddNTPs. Preferably the concentration is at least ten to twenty times higher. For example, if A is the mutant base and C is the wild-type base, during the SBE, we can use Rox-ddATP for the mutant, FITC-ddCTP for the wild type, ddGTP and ddTTP for blocking the nonspecific extension at the ratio of 1:2-10: 20:20. The unlabeled ddNTPs reduce nonspecific incorporation.

Another optional step for improving the specificity and/or sensitivity of the SBE reaction is to denature the double stranded nucleic acid duplexes attached to the beads prior to the SBE reaction. For example, the double strands can be heated or treated with sodium hydroxide. After the separation of the two strands, the single strands which are not bound to the beads can be separated from the beads and the bead-bound strands, and the single strands can be discarded.

Microemulsions can be formed according to any technique known in the art. Previously for BEAMing, a magnetic stirring bar was used to create microemulsions. Other means can also be used, including, without limitation, tissue homogenizers, whether mechanical or sonicator-type. Suitable mechanical homogenizers include rotor-stator type as well as blade type. Tissue homogenizers appear to form microemulsions of more uniform size than magnetic stirring bars.

If desired, yet another step of amplification can be used after the microemulsions are broken. This step typically employs isothermal amplification, also known as rolling circle amplification. In order to generate the rolling circle, a molecular inversion probe or a padlock probe can be used. They probe may require filling-in, or not, prior to a template-driven ligation reaction to generate a circle. If filling-in is required the region to be filled in will typically be from 1 to 30 nucleotides. The isothermal amplification can amplify the ultimately detected signal quite significantly. After isothermal amplification, a sequence feature can be detected using SBE (single base extension) reaction, as described above. Alternatively, the nucleotide sequence of the amplicon on the beads can be determined by any sequencing method known in the art, including sequencing-by-synthesis.

Samples which may be used as sources of analyte DNA include blood, plasma, urine, stool, sputum, tears, saliva, and bone marrow. Solid tissues can also provide analyte DNA. Samples can be obtained from cancer patients, from related family members, from pregnant women, and from neonates. Sources of analyte DNA may be treated, for example with test agents, and the effects of the test agents on the analyte DNA can be determined.

The data described in the examples conclusively demonstrate that APC gene fragments from the neoplastic cells of colorectal tumors can be found in the circulation and that the number of such fragments depends on tumor stage. These results have implications for both colorectal tumor biology and for practical diagnostic tests, as discussed below.

Previous studies have shown that the total DNA concentration in the plasma of cancer patients is often elevated (19, 20). Our results support this conclusion only in advanced stage patients, in that more total APC gene fragments (wild-type plus mutant) were present in the plasma of patients with Dukes' D cancers than in those with earlier stage tumors. Our results additionally show that this "extra" DNA in advanced stage patients is not derived from the neoplastic cells themselves, as only a minor fraction of the APC fragments are mutant whereas all the neoplastic cell's APC fragments are mutant.

But there are still a large number of mutant DNA fragments circulating in cancer patients. Assuming that the volume of distribution of DNA at steady state is similar to that of oligonucleotides in primates (60-70 ml/kg), an 8% fraction of mutant molecules among 47,800 fragments per ml plasma (as in Dukes' D patients) would correspond to $1.6 \times 10^7$ mutant fragments present in a 70 kg person at any given time (24). The half-life of this tumor DNA is estimated at 16 min based on the data obtained from clearance of fetal DNA in maternal plasma (25). This translates to ~6×10$^8$ mutant fragments released from the tumor each day. For patients with a tumor load of 100 g in size (~3×10$^{10}$ neoplastic cells), we thereby estimate that 3.3% of the tumor DNA is fed into the circulation on a daily basis. For a Dukes' B cancer of 30 g in which 1.3% of the 4000 circulating APC fragments per ml plasma are mutant, the corresponding estimate is that 0.15% of the tumor DNA is fed into the circulation each day.

Figure 5:
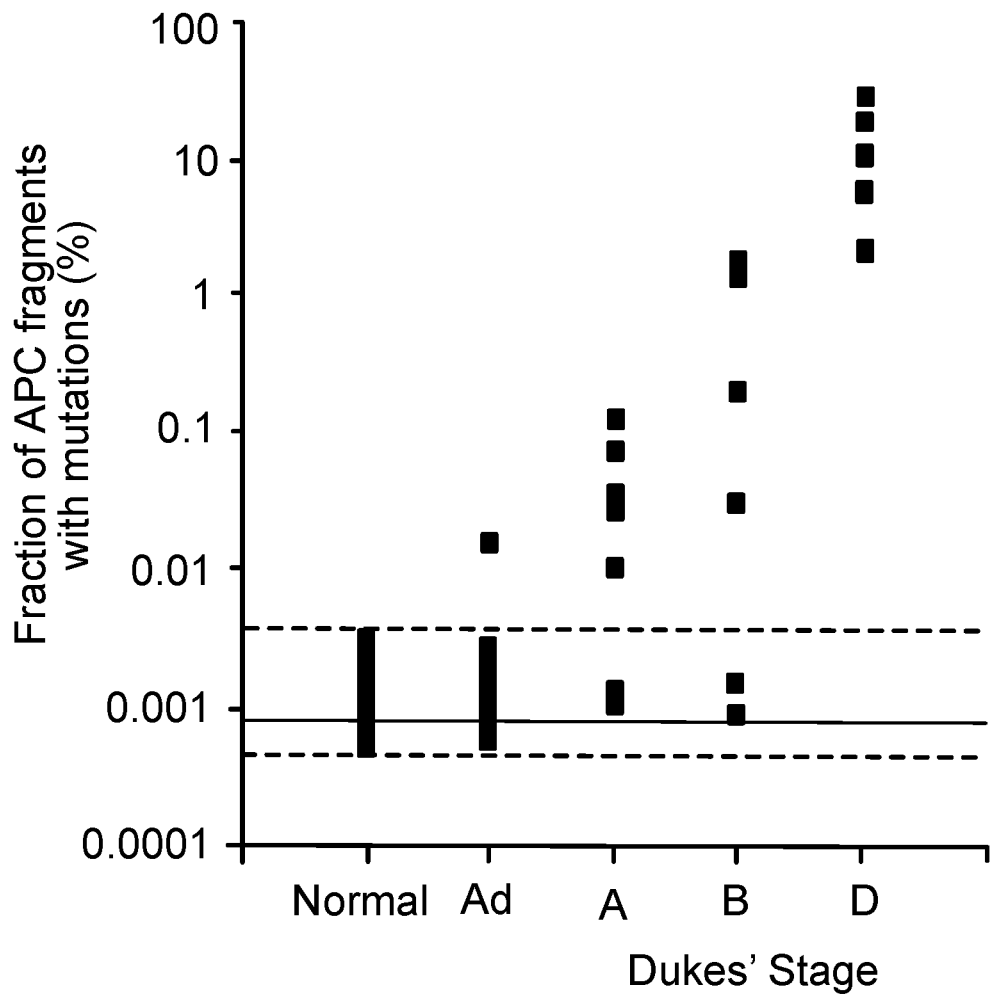
FIG. 5. Fraction of mutant APC gene fragments in the plasma of patients with various colorectal tumors (adenomas (Ad) and Dukes' stage A, B, and D carcinomas). In each mutation analyzed, DNA from normal lymphoid cells or plasma DNA from healthy donors were used as controls ("Normal"). The "mutants" observed in assays with normal cellular DNA represent errors generated during the PCR process rather than mutations present in the template DNA (see text). The red lines represent the mean, min, and max values of the normal controls.

So what is the source of this mutant DNA and how do mutant APC gene fragments get into the plasma? Several clues are provided by our data. The ability to get into the circulation was clearly not related to tumor size, as the benign tumors we studied were as large as the cancers (Table 4), yet the former rarely gave rise to detectable mutant DNA fragments. Similarly, the size of the cancers was not the critical parameter, as there was no significant correlation between the tumor load (including metastatic deposits) and the amount of mutant DNA in the circulation. On the other hand, the degree of invasion was indeed correlated with the number of circulating DNA fragments. Those lesions which weren't invasive (benign tumors) did not commonly feed mutant DNA molecules into the plasma. As tumors invaded through more layers of the intestinal wall in Dukes' B vs. Dukes' A tumors, and through the intestine to distant sites in Dukes' D vs. Dukes' B tumors, the number of circulating mutant DNA molecules progressively increased (FIG. 5).

Another clue is provided by the size of the mutant DNA molecules. The data in FIG. 1 show that mutant sequences are enriched in small DNA fragments and could not be identified at all in fragments of 1296 bp.

Based on these observations, we propose that the mutant DNA fragments found in the circulation are derived from necrotic neoplastic cells that had been engulfed by macrophages. As tumors enlarge and invade, they are more likely to outgrow their blood supply. Thus invasive tumors generally contain large regions of necrosis, while benign tumors rarely do (26-29). Necrotic cells are not thought to release DNA into the extracellular milieu (30). However, cells that die from necrosis or apoptosis are routinely phagocytosed by macrophages or other scavenger cells. Interestingly, it has been shown that macrophages that engulf necrotic cells release digested DNA into the medium, while macrophages that engulf apoptotic cells do not (30). Moreover, the size of the DNA released from macrophages is small (30). All of these observations are consistent with a model wherein hypoxia induces necrosis of tumors, leading to the phagocytosis of tumor cells and the subsequent release of the digested DNA into the circulation. As tumors become more aggressive, the degree of this necrosis increases and the absolute amount of circulating mutant DNA correspondingly rises. Because necrosis involves the killing not only of neoplastic cells, but also of surrounding stromal and inflammatory cells within the tumor, the DNA released from necrotic regions is likely to contain wild-type DNA sequences as well as mutant sequences. This may explain the increase in total (non-mutant) circulating DNA observed in the plasma of patients with advanced cancers.

The ability to detect and quantify mutant DNA molecules in the circulation has obvious clinical importance, and this line of research has been pursued by several investigators. Our results inform the field in several ways. First, it is unlikely that circulating mutant DNA could be used to detect pre-malignant tumors, based on the fact that we were unable to detect such DNA even in very large adenomas. Similarly, it is unlikely that loss of heterozygosity detection or other techniques that require a majority of the circulating DNA to be derived from neoplastic cells will allow such detection, as the proportion of mutant DNA fragments in plasma was small, averaging only 11% of the total DNA fragments even in large, metastatic cancers. We cannot easily reconcile our observations with previous data reporting the presence of large fractions of mutant DNA in the circulation, even from pre-malignant tumors. However, it is possible that tumors of organs other than the colon, on which several of the prior reports were based, behave differently with regards to their contribution to circulating DNA.

On the positive side, our data shows that even relatively early cancers give rise to circulating mutant DNA fragments that can be detected with sufficiently sensitive and specific assays. In fact, more than 60% of cancers that had not yet metastasized gave rise to detectable mutant fragments in plasma. Even Dukes' A tumors, which are by definition barely invasive, were detectable with BEAMing-based assays. Virtually all Dukes' A tumors and most Dukes' B tumors can be cured with conventional surgery alone, without the need for adjuvant therapies (31).

In practical terms, plasma-based assays for mutant DNA fragments are inferior in several ways to more conventional techniques for early colorectal cancer detection. Colonoscopy is the gold standard, with sensitivity rates >80% for adenomas and >90% for cancers (32). In particular, adenomas detected by colonoscopy can often be removed through the colonoscope, alleviating the need for surgery. Unfortunately, a variety of issues limit the widespread applicability of colonoscopy (either conventional or virtual) to the screening of asymptomatic patients (3, 5, 33). This has stimulated the development of non-invasive technologies. One of the most promising of these is the analysis of fecal DNA for mutations (34). Because of the frequent presence of mutant DNA molecules in feces from both adenomas and early cancers, fecal DNA analysis is superior to plasma with regards to sensitivity. However, plasma-based assays have potential advantages with regards to ease of implementation and compliance.

For many tumor types, there are currently no alternative methods for pre-symptomatic diagnosis, unlike the case with colorectal cancers. In these other tumor types, the evaluation of circulating DNA could be particularly useful. Even if such assays could detect only a fraction of patients with treatable cancers, much morbidity and mortality could be averted.

"BEAMing Up" represents an advance for the accurate detection and quantification of rare genetic variants in a population of DNA molecules. The approach provides robust signals and extremely high signal to noise ratios. As tens of millions of DNA template molecules can easily be analyzed by flow cytometry, its sensitivity for mutation detection is very high. In fact, its sensitivity is currently limited not by any intrinsic problem with the method itself but simply by the error rate of currently available polymerases used for PCR.

As the first application of this technology, we have determined the error rates of four polymerases representing representative types of commercially available PCR formulations. One was conventional *Thermus aquaticus* (Taq) polymerase, the second was Taq High Fidelity, a blend of Taq DNA Polymerase plus the proofreading enzyme *Pyrococcus* species GB-D containing a 3' to 5' exonuclease activity), the third was PfuUltra, a genetically engineered mutant of *Pyrococcus furiosus* (Pfu) DNA polymerase combined with a proprietary polymerase-enhancing factor, and the fourth was Phusion, a fusion protein consisting of a double stranded DNA binding domain and a Pfu-like polymerase.

Figure 8A:
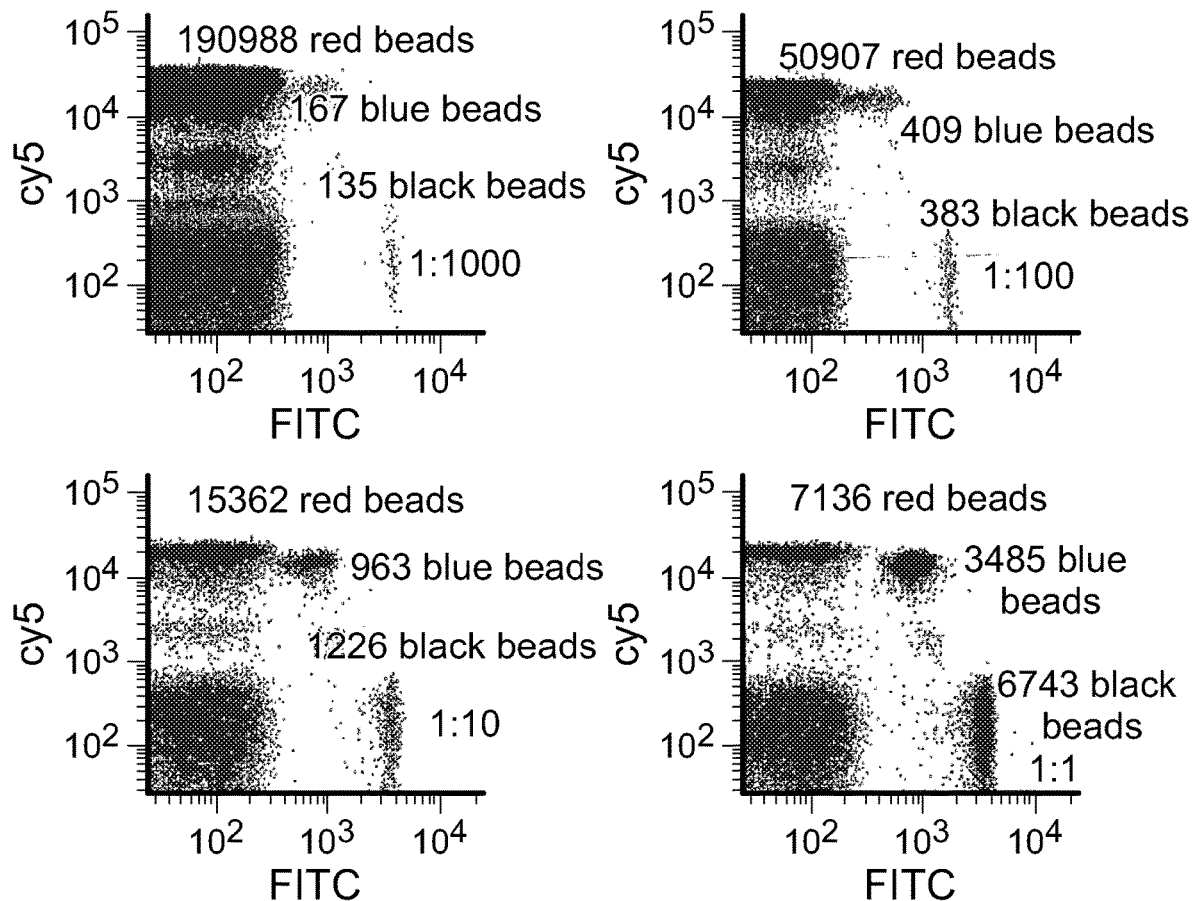
FIGS. 8A-8C: Quantification of different template ratios by BEAMing. PIK3CA amplicons were mixed with KRAS amplicons in a ratio of 1:1, 1:10, 1:100, and 1:1000 and used as templates for emulsion PCR.

It is interesting to try to compare our error determination results with those that are conventionally used for this purpose. For example, the supplier of Taq and Taq High Fidelity cloned PCR products produced by the two enzymes into plasmid vectors, then transforms bacteria with the plasmids. The mutation frequency was determined by dividing the total mutations by the total transformed cells. The error rate was determined by dividing the mutation frequency by the number of amino acids that can cause phenotypic changes in the two independent marker genes amplified (130 and 134 for rpsL and lacZ, respectively). The error rates for Taq using this assay were $4.2 \times 10^{-5}$ and $1.9 \times 10^{-5}$ epc for the rpsL and lacZ, respectively. These error rates were similar to those found we found for Taq ($2.3$-$3.4 \times 10^{-5}$ epc), despite the completely different nature of the sequences queried and the assays used. Note that the error rates determined by BEAMing are slight underestimates, as we ignore beads that have resulted from multi-template amplification (FIG. 8a). Our estimate for the relative fidelity of Taq High Fidelity was considerably different than those reported by the manufacturer, 1.3 to 1.7 times more accurate than Taq in our assays instead of 6 times more accurate.

The manufacturer of PfuUltra used a lad system similar to that described above, employing cloning of PCR products and phenotypic evaluation of colonies. They calculated an error rate of $4.3 \times 10^{-7}$ for PfuUltra and $1.4 \times 10^{-6}$ for Phusion. The manufacturer of Phusion used the same assay and found an error rate of $4.4 \times 10^{-7}$ epc for Pfhusion but $6.93 \times 10^{-7}$ for PfuUltra. We found that both PfuUltra and Phusion resulted in similar error rates (6.0 and $4.8 \times 10^{-7}$, respectively).

Some important points can be derived from these comparisons. First, the error rates determined with BEAMing Up are remarkably similar to those determined by conventional assays despite the huge differences between the sequences analyzed and the techniques used to measure mutations. Second, there are advantages to both approaches. Biological assays with lacZ, lacI, or rpsL provide averaged estimates of many different types of mutations across relatively large amplicons. In contrast, BEAMing-based assays provide error rates at specific positions. General statements about error rates of polymerases may best be supported either by conventional biologic assays (or by multiple BEAMing assays querying different positions of the same amplicon). But in many biomedical research applications, it is not the generalized error rate that determines the reliability of the experimental data but rather the mutation rate at the specific position analyzed. This is true, for example, in assays wherein specific mutations or methylation changes are queried in samples from cancer patients. Since DNA polymerase may have mutational spectrum bias and PCR noise may preferentially accumulate at hot spots (3, 4, 5), by including normal DNA as a negative control in BEAMing assays, the limit of sensitivity of the particular assay is reliably determined in a way that would be impossible with conventional approaches.

Finally, it is clear that the technique described here is considerably simpler and less time consuming than those historically used for error rate determinations. BEAMing Up eliminates the need for cloning, bacterial transformation, colony selection, and confirmation of mutations by sequencing of colonies. It also eliminates the need for assumptions about the number of residues that can be mutated to result in a specific phenotype and thereby provides a more direct measure of mutation frequency. It should prove useful for many types of experiments wherein the fidelity of processes related to replication or transcription is important. It should facilitate the identification of rare mutations in clinical samples. And because of the much higher amount of DNA per bead, the technique could be useful for increasing read length or accuracy of high throughput sequencing studies using DNA-bound beads as templates.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods for Examples 2-5
Sample Collection, DNA Extraction, and Sequencing.
Real-Time PCR Primers were designed to generate ~100 bp amplicons that included one or more mutation sites. A universal tag (5'-tcccgcgaaattaatacgac-3') was added to the 5' end of either the forward or reverse primer used to generate each amplicon. This universal tag was identical to the one bound to the beads used for BEAMing. The sequences of these primers are listed in Table 2, which is published as supporting information on the PNAS web site. PCR was performed in 50 µl reactions containing 10 µl 5× Phusion™ HF buffer, 0.2 mM of each dNTP, 1 µM of each primer, 1/50,000 dilution of SYBR® green I (Invitrogen), 1.5 U Phusion™ DNA polymerase (NEB, Beverly. Mass.), and 15 µl of purified plasma DNA (equivalent to 100 µl plasma) or genomic DNA purified from normal mononuclear cells of the blood of healthy volunteers. The amplifications were carried out with an iCycler PCR detection system (BioRad, Hercules, Calif.). PCR cycling conditions for all amplicons were as follows: 98° C. for 1 min; 3 cycles of 98° C. for 10 sec, 70° C. for 10 sec, 72° C. for 10 sec; 3 cycles of 98° C. for 10 sec, 67° C. for 10 sec, 72° C. for 10 sec; 3 cycles of 98° C. for 10 sec, 64° C. for 10 sec, 72° C. for 10 sec; 30 cycles of 98° C. for 10 sec, 61° C. for 10 sec, 72° C. for 10 sec. Each reaction was performed in duplicate and a calibration curve was generated in each 96 well plate using various amounts of normal human genomic DNA. The concentration of PCR products was determined using a PicoGreen™ dsDNA quantification assay (Invitrogen).
BEAMing A common oligonucleotide (5'-tcccgcgaaattaatacgac-3') was synthesized with a dual biotin group at the 5' end and with a six carbon linker (C6) between the biotin and the other nucleotides (IDT, Coralville, Iowa). This oligonucleotide was coupled to streptavidin-coated magnetic beads (MyOne™, Dynal, Oslo, Norway) according to the protocol published previously (16). The water-in-oil emulsions were prepared by modifications of the method described by Ghadessy and Holliger (17) using a homogenization protocol originally described by Bernath et al. (18). For each emulsion PCR, a 240 µl aliquot of an aqueous PCR mix was added to 960 µl of 7% (w/v) Abil® EM90 (Degussa—Goldschmidt Chemical, Hopewell, Va.) in mineral oil (M3516; Sigma). The aqueous phase contained 67 mM Tris-HCl pH 8.8, 16.6 mM $(NH_4)_2SO_4$, 6.7 mM $MgCl_2$, 10 mM 2-mercaptoethanol, 0.2 mM of each dNTP, 0.05 µM forward primer (5'-tcccgcgaaattaatacgac-3') and 8 µM reverse primer, 0.2 U/µl Platinum® Taq polymerase (Invitrogen), $3 \times 10^5$/µl oligonucleotide-coupled beads and 0.1 pg/μl template DNA. The reverse primers are listed in Table 2, which is published as supporting information on the PNAS web site. The water-oil mix was vortexed for 10 sec then emulsified for 50 sec using an Ultra-Turrax® homogenizer (T25 basic; IKA, Wilmington, N.C.) with a disposable OmniTip™ (Omni International Inc., Marietta, Ga.) at the minimum speed. The emulsions were aliquoted into eight wells of a 96-well PCR plate and cycled under the following conditions: 94° C. for 2 min; 50 cycles of 94° C. for 10 sec, 58° C. for 15 sec, and 70° C. for 15 sec. After PCR, the emulsions were pooled into a 15 ml tube and demulsified through the addition of 10 ml of NX buffer (100 mM NaCl, 1% Triton X-100, 10 mM Tris-HCl pH 7.5, 1 mM EDTA, 1% SDS). After vortexing for 10 sec, the beads were pelleted by centrifugation for 5 min at 4,100 g. The top phase was removed and the beads were resuspended in 800 μl NX buffer and transferred to a 1.5 ml tube. The beads were collected using a magnet (MPC-S, Dynal) and washed with 800 μl wash buffer (20 mM Tris-HCl, pH 8.4, 50 mM KCl). The double-stranded DNA on the beads was converted to single-stranded DNA by incubation in 800 μl 0.1 M NaOH for 2 min at room temperature. The beads were washed twice with 800 μl wash buffer using the magnet and finally resuspended in 200 μl of wash buffer. Single base extension and flow cytometry were performed as described in supporting information published on the PNAS web site.

Sample Collection and DNA Extraction

Tissue samples, matched blood samples and clinical data were collected by Indivumed from surgical patients of the Israelitic Hospital and the Clinic Alten Eichen (both in Hamburg, Germany) following strictly controlled SOP criteria. IRB approval was given by the Ethical-board of the Physicians Association of Hamburg, Germany and patients' samples and data were collected after obtaining informed and written consent. The samples used in the current study were randomly chosen from those contributing through this protocol. Shortly before surgery, 18 ml EDTA blood was taken from a central catheter, chilled to 8° C. immediately, and transported to the lab within 30 minutes for plasma preparation. The blood cells were pelleted for 15 min at 200 g in a Leucosep®-tube (Greiner, Frickenhausen, Germany) filled with 15 ml Ficoll-Paque solution. After centrifugation the supernatant (i.e., plasma) was transferred into 1.5 ml tubes, immediately frozen, and stored at −80° C. The plasma samples were thawed at room temperature for 5 min and any remaining debris pelleted at 16,000 g for 5 min. The supernatant was transferred to a new tube and digested with 500 μg/ml proteinase K (Invitrogen, Carlsbad, Calif.) in 2.5 mM Tris-HCl, 0.25 mM EDTA pH 7.5, and 1% SDS overnight. The DNA was extracted twice with phenol-chloroform (VWR, Cat # IB05174) and precipitated with two volumes ethanol in the presence of 3.3 M ammonium acetate and 3.3% (v/v) seeDNA™ (GE Healthcare, Piscataway, N.J.). The DNA from 1 ml plasma was dissolved in 150 μl of 10 mM Tris-HCl, 1 mM EDTA. pH 7.5. Tumor DNA was purified with the DNeasy tissue kit (Qiagen, Valencia, Calif.) according to the manufacturer's instructions.

Digital PCR and DNA Sequencing

Digital PCR followed by direct sequencing of PCR products generated from single template molecules was used to determine the APC mutation status of the primary colon tumors and to analyze plasma DNA fragments of different sizes.

Tumor DNA was diluted in 96 well PCR plates so that one or two template molecules were contained within each 10 μl reaction. To obtain a robust and uniform amplification, nested PCR reactions were performed. The first amplification comprised a 1296 bp region of the APC mutation cluster region (F1 5'-ACGTCATGTGGATCAGCCTATTG-3'; R1 5'-GGTAATTTTGAAGCAGTCTGGGC-3'). The second amplification was split into two separate PCR reactions (A and B), with each one including half of this region (primers for A: F2 A 5'-TCTGGACAAAGCAGTAAAACCG-3'; R2 A 5'-CTTGGTGGCATGGTTTGTC-3'; primers for B: F2 B 5'-GCTCAGACACCCAAAAGTCC-3'; R2 B 5'-ACGTGATGACTTTGTTGGCATGGC-3'). The PCR mix contained 1×PCR buffer, 1 μM of each oligonucleotide, 1 mM of each dNTP, 6% DMSO, and 0.05 U/μl Platinum® Taq polymerase (Invitrogen). The following temperature profile was used for the amplification: 94° C. for 2 min; 3 cycles of 94° C. for 30 s, 67° C. for 30 s, 70° C. for 1 min; 3 cycles of 94° C. for 30 s, 64° C. for 30 s, 70° C. for 1 min, 3 cycles of 94° C. for 30 s, 61° C. for 30 s, 70° C. for 1 min; 50 cycles of 94° C. for 30 s, 61° C. for 30 s, 70° C. for 1 min. One μl of the first amplification was added to each of the second 10 μl PCR reactions. The second PCR employed the following cycling conditions: 2 min at 94° C.; 15 cycles of 94° C. for 30 s, 58° C. for 30 s, 70° C. for 1 min. The PCR products were purified using the AMpure® PCR purification system (Agencourt, Beverly Mass.) and sequencing reactions were performed with BigDye® Terminator v3.1 (Applied Biosystems, Foster City, Calif.). Sequencing reactions were resolved on an automated 384 capillary DNA sequencer (Spectrumedix, State College, Pa.). Data analysis was performed using the Mutation Explorer® package (SoftGenetics, State College, Pa.). Of 12 relatively large adenomas (>1 cm), 11 were found to contain APC mutations within the region analyzed. Of 34 patients with Dukes' A or B carcinomas, 16 were found to contain APC gene mutations, and of 10 patients with Dukes' D carcinomas, 6 were found to contain APC gene mutations. Plasma was obtained from these 33 patients for analysis of circulating DNA, as described in Results.

For analysis of the size spectrum of plasma DNA in three patients with advanced cancers, digital PCR was performed as above for tumor DNA except that primers yielding amplicons of different sizes were used (primer sequences are listed in Table 1, which is published as supporting information on the PNAS web site). The reaction components and temperature cycling conditions for the first and second PCR were the same as described above except that the extension time was cut in half for fragments smaller than 500 bp. Agarose gel electrophoresis of the PCR products from each well was used to count the total number of APC templates contained in various dilutions of plasma DNA. These same PCR products were used in sequencing reactions to determine the number of templates containing mutant APC sequences, as described above.

Single Base Extension (SBE)

Single base extension reactions were performed in 80 μl of 1×SBE buffer (150 mM Tris-HCl pH 9.5, 67 mM MgCl$_2$) containing 3×10$^6$ magnetic beads from the emulsion PCR, 2.5 μM FITC-labeled ddATP (Perkin-Elmer, Wellesley, Mass.), 3.5 μM Cy5-labeled ddGTP (GE Healthcare), 25 μM of unlabeled ddCTP and ddUTP (USB, Cleveland, Ohio), 0.3 μM biotinylated primer, 20 U/μl ThermoSequenase™ (GE Healthcare). The primers used for SBE are listed in Table 3, which is published as supporting information on the PNAS web site. This composition was used when the wild-type sequence at the queried position was G and mutant sequence was A; appropriate substitutions for the indicated ddNTPs were made when other bases were queried. Also note that the streptavidin present on MyOne™ beads is denatured during the emulsion PCR and does not bind biotin thereafter, so the primer used for SBE only binds to extended PCR products via hybridization and not to the beads themselves. The reactions were carried out at 94° C. for 2 min, 65° C. for 1 min, and 70° C. for 2 min. After the extension reaction, the beads were recovered by magnetic separation, washed once with 200 µl wash buffer and once with 200 µl wash buffer plus 0.1% BSA, and then resuspended in 180 µl of binding buffer (5 mM Tris-HCl pH 7.5, 0.5 mM EDTA, 1 M NaCl). The beads were mixed with 20 µl of 10 µg/ml streptavidin-conjugated phycoerythrin (PE, Invitrogen) to label the biotin-conjugated primer and incubated at room temperature for 10 min. The beads were recovered with the magnet and washed twice with 200 µl wash buffer, then resuspended in 400 µl wash buffer.

Flow Cytometry

Beads were analyzed with a LSR II flow cytometer or sorted with a FACSAria™ (both from BD Biosciences, San Jose, Calif.). The flow rate was typically set at 5000 events per second and a minimum of $2 \times 10^6$ events for each bead population was collected. These events were gated to exclude doublets and other aggregates. For the calculations of mutant frequency, only single beads with a PE signal at least 10-fold above the mean background signal were considered. In selected cases, beads were recovered by flow sorting and individual beads used in sequencing reactions. This was accomplished by first diluting the sorted beads in 96 well PCR plates so that one of every two wells (on average) contained a bead. The single-stranded DNA bound to each bead was then converted to double-stranded DNA by a DNA polymerase and released by a restriction enzyme digest that only cleaved the universal primer sequence on the beads. The DNA polymerase reaction was performed in a volume of 2 µl under a layer of mineral oil and contained 1×PCR buffer, 1 µM of the reverse oligonucleotide used for BEAMing, 1 mM of each dNTP and 0.05 U/µl Platinum® Taq polymerase. The following temperature profile was used for the Taq polymerization: 95° C. for 2 min, 58° C. for 15 s, and 70° C. for 1 min. Three µl of a mix containing 0.5 µl 10× buffer 3 (NEB), and 0.04 µl 10 U/µl Ase I (NEB) was added to the polymerase reaction and incubated at 37° C. for 30 min. The entire 5 µl reaction was then used as template for a 25 µl PCR reaction. The reaction components were the same as for the Taq polymerization except that the two primers used for the emulsion PCR were included (Table 2, which is published as supporting information on the PNAS web site). The PCR products were purified with AMpure® and sequenced, as described above (Digital PCR and DNA sequencing).

Example 2

Circulating Mutant DNA is Degraded.

We used real-time PCR or digital PCR to determine the number of total circulating APC genes in 33 patients with colorectal tumors and ten age-matched donors without any tumor. The number of APC gene copies was significantly higher in advanced stage patients (Dukes' D) than in patients with early stage cancers (p<0.0001, Student's t-Test), consistent with previous studies (19, 20). In advanced stage patients, the median number of APC gene fragments per ml plasma was 47,800 while the median number was 3,500 and 4,000 for patients with Dukes' A and Dukes' B cancers, respectively (Table 4). There was no significant difference between the number of circulating copies in early stage cancer patients (Duke's A or B), patients with adenomas (4300 APC fragments/ml plasma) and normal individuals (3460 APC fragment/ml plasma; range 1150 to 8280 fragments/ml). There also appeared to be little difference between the number of APC fragments determined by these assays when the position of the amplicons within APC was varied (data not shown).

Figure 1B:
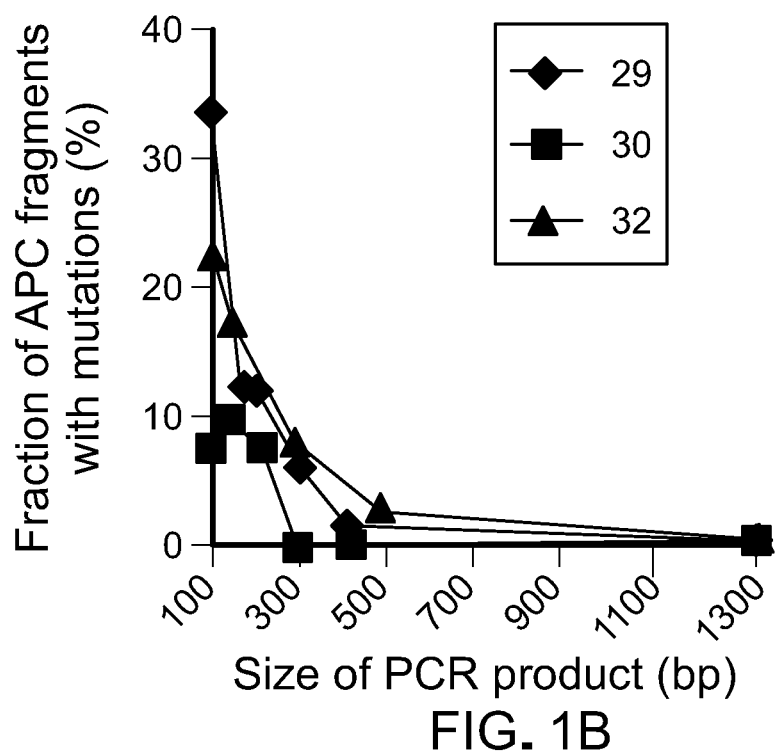

To determine the size of mutant gene fragments in circulating DNA, we analyzed plasma DNA from three patients with advanced colorectal cancers (Dukes' D, metastatic to liver) who were shown to contain APC gene mutations in their tumors. By varying the size of the amplicons generated by PCR, it was possible to determine the number of normal and mutant gene fragments present in plasma by sequencing PCR products derived from one or a few template molecules (Digital PCR, as described in Materials and Methods). The size of the amplicons varied from 100 to 1296 bp and encompassed the mutation present in each patient. The number of total APC fragments (wild-type plus mutant) increased by 5 to 20 fold as the size of the amplicons decreased from 1296 to 100 bp (FIG. 1A). The fraction of mutant molecules was strikingly dependent on size of the amplicon, increasing by more than 100 fold over the size range tested (FIG. 1B). For example, though APC fragments of >1296 bp could be identified in the plasma of all three patients, there were no mutant APC sequences found in ~1000 fragments of this size. With very small amplicons (~100 bp), at least 8% of the plasma APC gene fragments were found to be mutant in all three patients.

We conclude that the mutant DNA fragments present in the circulation of cancer patients are degraded compared to the circulating DNA derived from non-neoplastic cells. This conclusion is consistent with previous studies of other tumor types (21, 22) and has important implications for the detection of such mutant molecules. In particular, small amplicons can be used to enrich for DNA sequences derived from cancer cells.

Example 3

Development of a Quantitative Assay for Detection of Rare Mutations

Figure 2A:
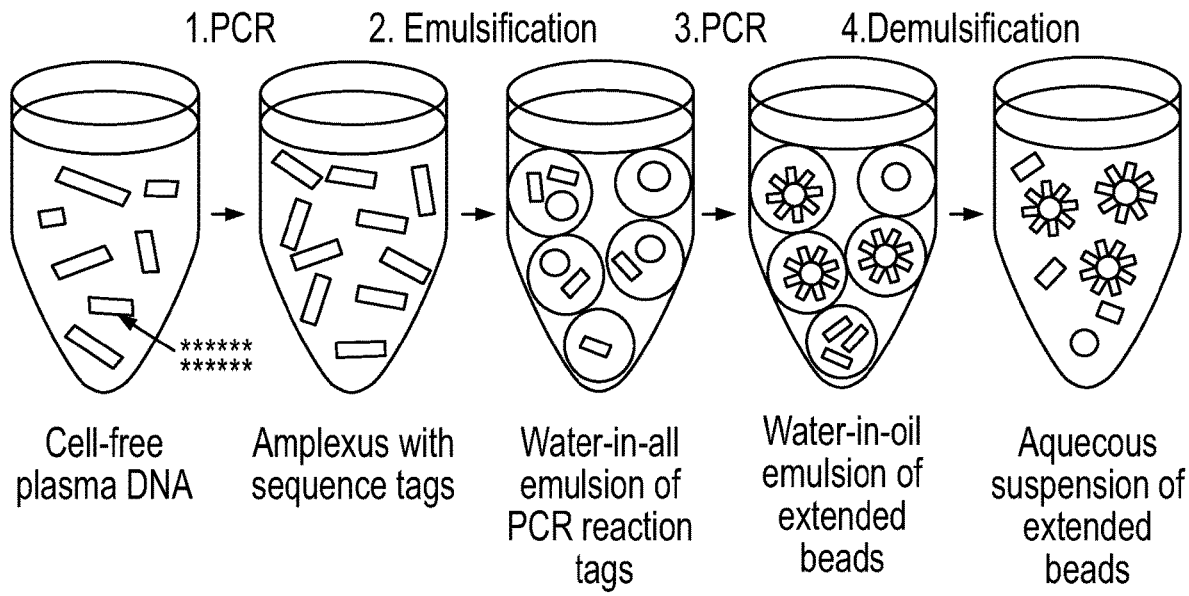
FIGS. 2A-2B. Schematic of the BEAM-based assay.
Figure 2B:
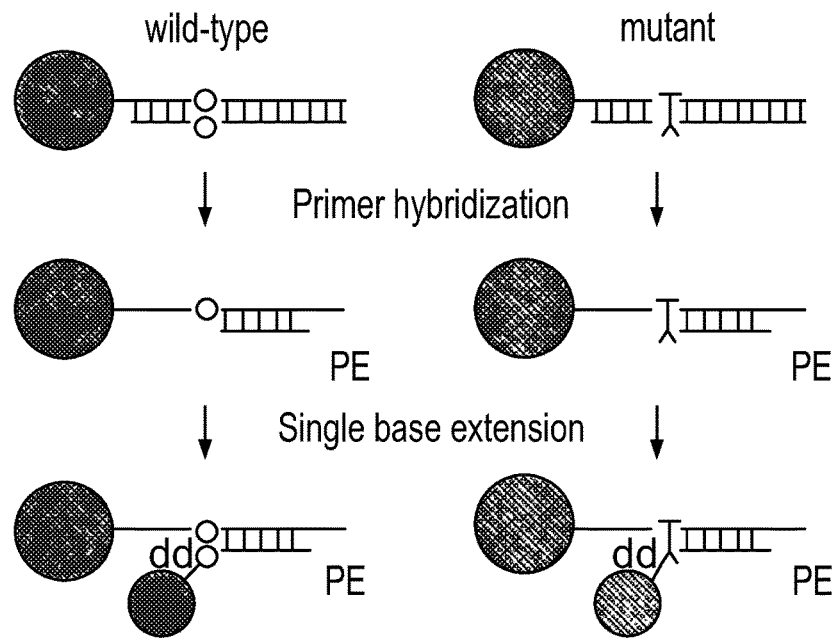
Figure 4A:
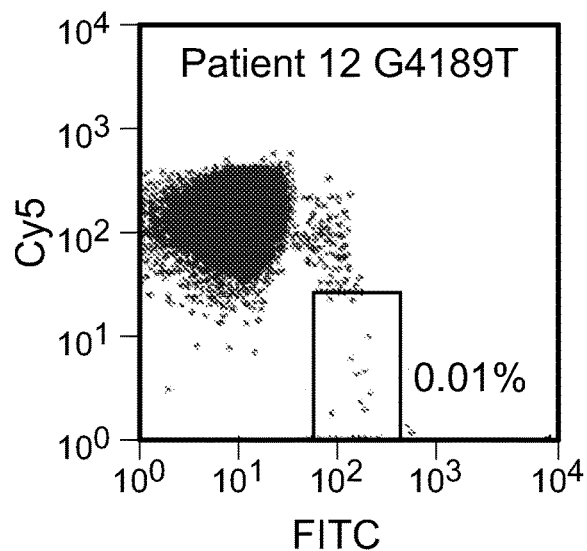
FIGS. 4A-4D. Examples of flow cytometric profiles of beads generated from plasma DNA. Cy5 and FITC fluorescence intensity profiles of PE-positive beads from four patients are shown. The patients, mutations, and fraction of mutant APC fragments are indicated.
Figure 4B:
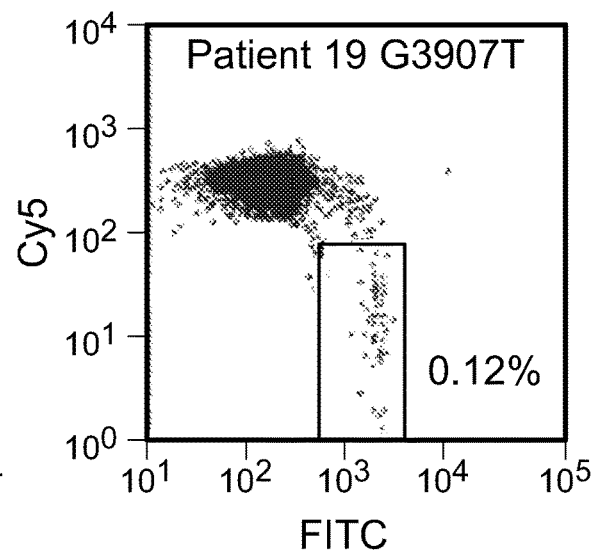
Figure 4C:
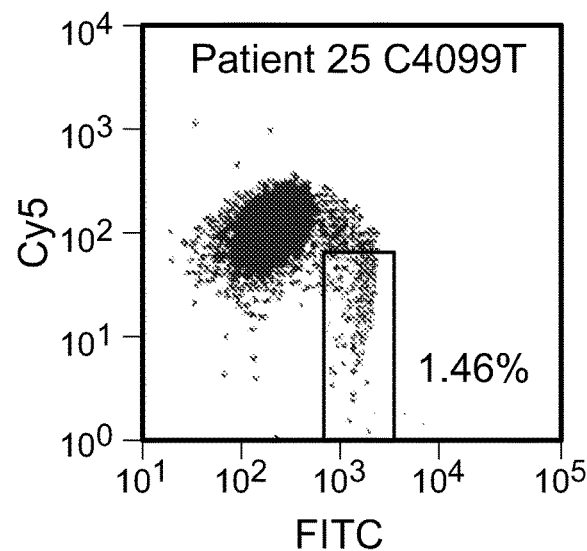
Figure 4D:
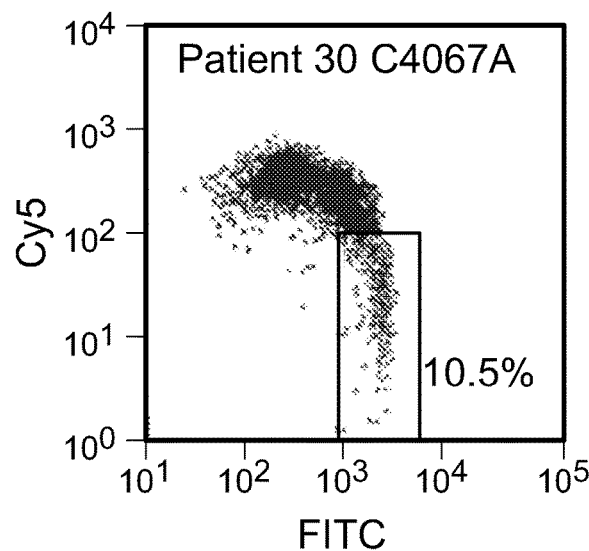

The results described above were obtained by sequencing hundreds of PCR products each derived from one or a few DNA template molecules. In preliminary studies, we found that such Digital PCR-based techniques were sufficiently sensitive to detect circulating mutant DNA molecules in patients with advanced cancers, but not in patients with early stage cancers. To increase the sensitivity and reliability of these assays, we developed an extension of BEAMing that allowed us to examine many more template molecules in a convenient fashion. The approach consists of four steps: (i) Real-time PCR was used to determine the number of APC gene fragments in the plasma sample (FIG. 2A, step 1); (ii) BEAMing was used to convert the amplified plasma DNA into a population of beads (FIG. 2A step 2-4); (iii) the mutational status of the extended beads was determined by single base extension (FIG. 2B); and (iv) flow cytometry was used to simultaneously measure the FITC, Cy5, and PE signals of individual beads.

FIG. 3 shows a representative flow cytometry result wherein the interpretation of the profiles was confirmed experimentally. In the example shown, a total of 342,573 beads were analyzed by flow cytometry. The single bead population (295,645) was used for fluorescence analysis (FIG. 3A). Of these, 30,236 exhibited a PE signal (FIG. 3B), indicating that they had been extended during the emulsion PCR. The FITC and Cy5 signals reflected the number of beads containing mutant or wild-type sequences, respectively. Beads containing the wild-type DNA sequences (30,186) had high Cy5 but background FITC signal ("red beads" in FIG. 3C). Beads extended only with mutant DNA sequences (22) had high FITC signals but background Cy5 signals ("green beads"). Twenty-eight had both FITC and Cy5 signals ("blue beads"). Such dual-labeled beads resulted from either the presence of both a wild-type and mutant template in the droplet containing the bead or an error in the early cycles of the emulsion PCR (see below). These dual-labeled beads were eliminated from analysis, and only homogenously-labeled beads were considered for the enumeration of mutations. Note that this conservative analysis strategy results in a slight underestimation of the fraction of mutations, as it excludes mutants that were present in droplets that also contained one or more wt fragments. Beads in each of these three populations were collected by flow sorting and single beads from the sort were used as templates in conventional DNA sequencing. All 131 beads subjected to sequencing analysis showed the expected patterns, with examples illustrated in FIG. 3C.

Example 4

Limits to the Sensitivity of Assays for Plasma DNA Mutations

The results described above show that the BEAMing approach can, in principle, detect a very small fraction of fragments containing mutant sequences within a much larger pool of fragments containing wild-type sequence. Because >50 million beads are used in a single emulsion PCR and flow cytometry can be performed at speeds of >50,000 beads per sec, the capacity to enumerate such mutations is not limited by the beads themselves. Instead, two other features limit the sensitivity. First, there is a finite number of DNA fragments present in clinical samples. As noted above, this number ranged from 1,350 to 230,000 fragments per ml in the patients with tumors (Table 4) and from 1150 to 8280 fragments/ml in control patients. This gives an upper bound to the sensitivity of the assays. For example, a calculation using the Poisson distribution shows that if 4000 fragments were analyzed, the mutation frequency would have to be greater than 1 in 1333 fragments (i.e., 3 divided by the number of total fragments analyzed) for the assay to achieve 95% sensitivity. A second limiting feature is the error rates of the polymerases used for PCR. In our approach, two PCR steps are employed: The first is a conventional PCR that employs plasma DNA fragments as templates and the second is an oil-in-water emulsion PCR that uses the initial PCR products as templates. In the emulsion PCR, errors occurring during the early rounds of PCR can result in heterogeneous beads containing both wild-type and mutant sequences. These are easily eliminated from consideration, as described in FIG. 3C. However, the errors introduced in the first PCR cannot be eliminated, as they give rise to beads with homogeneous mutant sequences, indistinguishable from those resulting from genuine mutations in the original plasma DNA templates.

The fraction of mutant molecules present after the first PCR equals the product of the mutation rate of the polymerase and the number of cycles carried out. BEAMing provides a quantitative way to determine the error rate of any polymerase used in PCR, without requiring cloning in bacterial vectors (Li et al., unpublished data). Of 19 different base changes evaluated in normal DNA, the error rates with the polymerase used in the current study averaged $3.0 \times 10^{-7}$ mutations/bp/PCR cycle and ranged from $1.7 \times 10^{-7}$ to $6.5 \times 10^{-7}$ mutations/bp/PCR cycle, depending on the mutation site assessed. As a result, we only scored plasma samples as positive for mutations if their frequency in the sample was significantly higher than the maximum error rate of polymerase found experimentally (i.e., $1.95 \times 10^{-5}$ after 30 cycles). As a result of the relatively low error rate with the polymerase used, it was the number of molecules present in the original plasma sample, rather than the polymerase error rate per se, that limited sensitivity.

These issues suggest that the sensitivity of assays for circulating mutant DNA could be increased in the future by (i) the development of new or modified polymerases with reduced error rates and (ii) the use of more plasma per assay (i.e., more template molecules).

Example 5

Quantification of Mutant APC Fragments in Plasma from Patients with Colorectal Tumors Based on the principles derived from the experiments described above, we determined whether fragments of tumor DNA could be detected in patients with colorectal tumors of various types. We selected APC gene mutations for this assessment, as >85% of colorectal tumors contain mutations of this gene, irrespective of tumor stage (23). Mutations in the mutation cluster region were evaluated by sequencing of DNA purified from the tumors of 56 patients. Mutations were observed in 33 of these patients (59%), and as expected, the proportion of tumors with these mutations did not differ significantly among tumors of various stages (see Materials and Methods).

A BEAMing assay was then designed for each of the mutations identified in the 33 tumors and applied to the DNA purified from the plasma of the corresponding patients (Table 4). In each case, DNA from normal lymphocytes or plasma from patients without cancer were used as negative controls. DNA from the tumors of the 33 patients was used as positive controls. All six patients with advanced lesions (Dukes' D, defined as having at least one distant metastatic lesion) were found to contain mutant DNA fragments in their plasma. Among 16 patients harboring cancers with a favorable prognosis (Dukes' A or B, defined as having no lymph node involvement and no distant metastases), ten (63%) were found to contain mutant DNA fragments in their plasma. In contrast, among 11 patients with large, benign tumors (adenomas), only 1 patient's plasma was found to contain mutant DNA fragments. Representative flow cytometric results are shown in FIG. 4 and summarized in Table 4.

The fraction of mutant molecules found in the plasma of the 17 cases with detectable mutations also varied according to tumor stage (p<0.0001, Fisher Exact test). In the advanced cases (Dukes' D), an average of 11.1% (range 1.9% to 27%) of the total APC gene fragments were mutant. In patients without metastases (Dukes' B), an average of 0.9% (range 0.03% to 1.75%) of the plasma APC gene fragments were mutant. In patients with lower stage tumors (Dukes' A), the fraction was even lower, averaging 0.04% (range 0.01% to 0.12%). And in the one patient with a benign tumor, only 0.02% of the plasma DNA fragments were mutant. The median fraction of positive beads found in the control DNA samples from patients without cancer was 0.0009% (range 0.003% to 0.0005%).

Table 4 also lists the concentration of total APC fragments (wild-type plus mutant) in these patients' plasma. There was no direct relationship between the concentration of total APC fragments and the mutational load. Though patients with advanced cancers tended to have higher concentrations of total APC fragments than the other patients, this increase was not due to DNA from neoplastic cells. Furthermore, no correlation was found between tumor burden (volume of primary tumor plus metastatic sites) and either the concentration of APC fragments or percentage of mutant APC fragments in the circulation.

Example 6

Overview

The approach described here entails four major steps (FIG. 5).

Step 1. PCR amplification from DNA samples.

Step 2. BEAMing. Oil-in-water (w/o) emulsions are formed in which single DNA molecules within each aqueous compartment are amplified and bound to beads.

Step 3, Filling gaps. A padlock (6) or cirularizable probe (7, 8) was hybridized to the sequences on the beads. A 0-30 bp gap was filled in with a polymerase and the ends ligated.

Step 4. Rolling circle amplification. Sequences to be queried on the beads are further amplified through rolling circle amplification.

Step 5. Single base extension. Fluorescently-labeled dideoxy nucleotide terminators are used to distinguish beads containing sequences that diverge at positions of interest.

Step 6. Flow cytometry. The population of beads is analyzed to determine the proportions containing each sequence of interest.

Materials and Methods for Examples 6-9:

Amplification of Human Genomic DNA

Phusion™ DNA polymerase (NEB) was used for the initial amplification of genomic DNA unless otherwise indicated in the text. Primers were designed to generate amplicons of 100 bp. A universal tag (5'-tcccgcgaaattaatacgac-3'), the sequence of which was identical to the one coated on the beads used for BEAMing, was added to the 5' end of the forward or reverse primer. PCR was performed in 50 ul reactions containing 10 µl 5× Phusion™ HF buffer, 0.2 mM of each dNTP, 1 µM of each primer, 1.5 U Phusion™ DNA polymerase (NEB), and 15 µl purified cell line DNA. PCR cycling conditions were as follows: 98° C. for 1 min; 3 cycles of 98° C. for 10 sec, 70° C. for 10 sec, 72° C. for 10 sec; 3 cycles of 98° C. for 10 sec, 67° C. for 10 sec, 72° C. for 10 sec; 3 cycles of 98° C. for 10 sec, 64° C. for 10 sec, 72° C. for 10 sec; 30 cycles of 98° C. for 10 sec, 61° C. for 10 sec, 72° C. for 10 sec. The amount of PCR product was quantified by using a PicoGreen™ dsDNA quantification kit (Invitrogen).

BEAMing

An oligonucleotide labeled at its 5' end with a dual biotin group was coupled to streptavidin-coated 1 micron magnetic beads (Dynal MyOne™) as described in Dressman et al. A 240 ul PCR mixture was prepared and added to 960 µl of 7% (w/v) Abil® EM90 (Degussa AG) in mineral oil (Sigma). The PCR mixture contained 67 mM Tris-HCl pH 8.8, 16.6 mM (NH4)2SO4, 6.7 mM MgCl2, 10 mM 2-mercaptoethanol, 0.2 mM of each dNTP, 0.05 µM of forward primer identical in sequence to the universal tag described above, 8 µM reverse primer, 0.2 U/µl Platinum® Taq polymerase (Invitrogen), 10×108 oligonucleotide coupled beads and ~20 pg template DNA. The water-oil mixture was vortexed for 10 sec at maximum speed (Vortex Genie 2) and then emulsified for 50 sec using an Ultra-Turrax homogenizer (T25) with a disposable OmniTip (Omni International, Inc.) at the minimum speed. The emulsions were transferred to a 96 well PCR plate, using 100 ul/well. The PCR cycling conditions were 94° C. for 2 min; 50 cycles of 94° C. for 10 sec, 58° C. for 15 sec, and 70° C. for 15 sec. After PCR, the emulsion was broken in 10 ml NX-SDS buffer (100 mM NaCl, 1% Triton X-100, 10 mM Tris-HCl pH 7.5, 1 mM EDTA, 1% SDS) by centrifugation for 5 min at 4,500 g. The beads were then incubated with 0.1 M NaOH for 2 min to remove the non-biotinylated strand of the PCR product, collected with a magnet, and resuspended in 1×PCR buffer.

Rolling Circle Amplification on the Beads

A padlock probe (100 nM) was hybridized to ~$10^7$ beads in 2×SSC, 20% formamide and 0.5 ug/ul sonicated salmon sperm DNA at 37° C. for 15 minutes. Probe was ligated in 10 U/µl T4 DNA ligase (NEB), 10 mM Tris-acetate pH 7.5, 10 mM MgAc2, 250 mM NaCl, 1 mM ATP and 0.2 ug/ul BSA at 37° C. for 15 min. Beads were then resuspended in 100 ul of 1×φ29 DNA polymerase reaction buffer (NEB), 0.1 ug/ul BSA and 0.3 mM dNTP mixture containing 1 U/ul Phi29 DNA polymerase (NEB) and incubated at 37° C. from 5 min to 6 hr.

Gap-Filling Rolling Circle Amplification on the Beads

A circularizable probe (150 nM) was hybridized to ~$10^7$ beads in Ampligase 1× Ampligase reaction buffer (Epicentre) at 55° C. for 15 min. Then, 50 µM dNTP (USB), 0.05 U/ul Stoffel fragment DNA (Applied Biosystems) and 1 U/ul Ampligase were added and extension plus ligation performed at 55° C. for 30 min. Beads were then resuspended in 100 ul of 1×φ29 DNA polymerase reaction buffer (NEB), 0.1 ug/ul BSA and 0.3 mM dNTP mixture containing 1 U/ul Phi29 DNA polymerase (NEB) and incubated at 37° C. for 1 hr unless indicated otherwise in the text.

Detection of Amplified DNA on Beads

To detect the presence of amplified sequences on beads, a fluorescein-labeled oligonucleotide complementary to the sequences amplified during the RCA was hybridized to the beads in SBE buffer (150 mM Tris-HCl pH 9.5, 67 mM MgCl2, 5% formamide) at 50° C. for 15 minutes.

To detect specific genetic mutations on the amplified DNA attached to beads, single base extensions (SBE) were performed in 150 ul SBE buffer containing $10^7$ beads, a 250 nM Cy5-labeled SBE primer, 5 µM FITC-labeled ddNTP (Perkin-Elmer), 0.25 µM Rox-labeled ddNTP (Perkin-Elmer), 10 uM of each unlabeled ddNTP (USB), and 0.4 U/µl ThermoSequenase™ (GE Healthcare) at 50° C. for 15 min. Beads were then resuspended in 200 ul 10 mM Tris, pH 7.5, 1 mM EDTA, pH 7.5.

Flow Cytometry

Beads were analyzed with a LSR II flow cytometer and data were analyzed with FACSDiva™ software (BD Biosciences). The flow rate was typically set at 5000-10,000 events per second. Events were gated to exclude doublets and aggregates. For the calculations of mutant frequency, only single beads exhibiting hybridization to the SBE primer were considered.

Example 7

BEAMing

Figure 7:
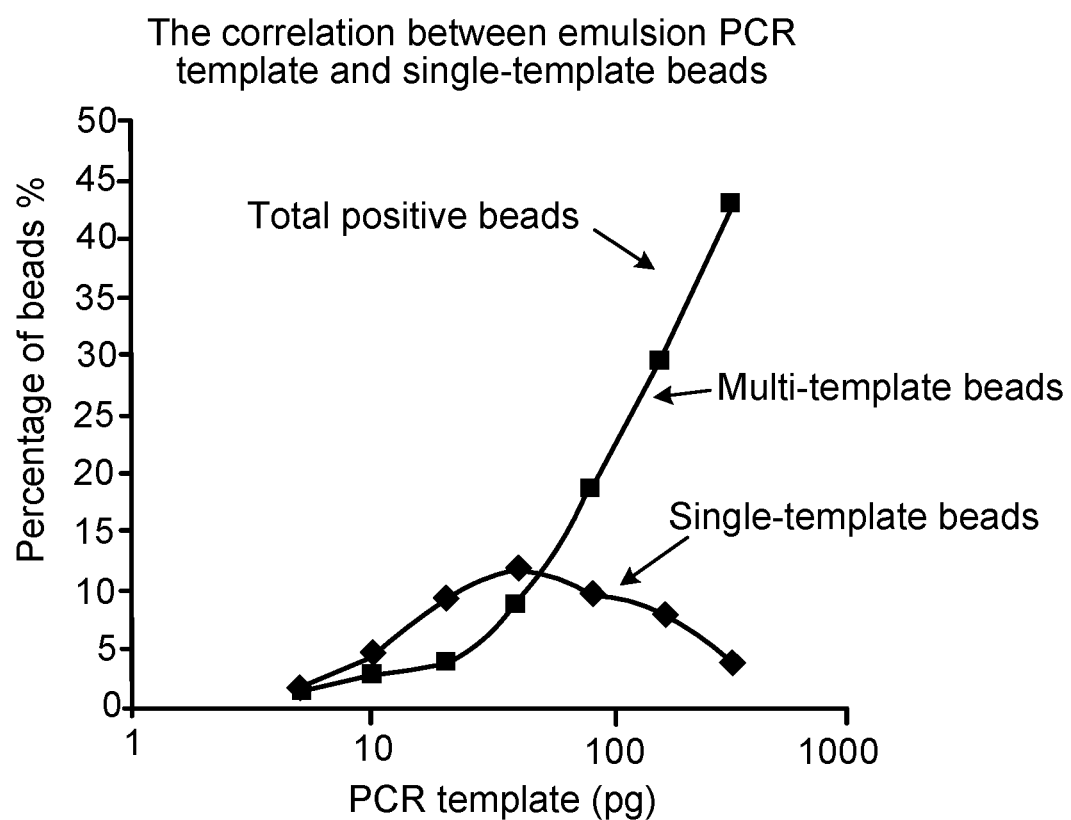
FIG. 7: Correlation between the total amount of template DNA per emulsion PCR and the fraction of emulsions that contain a single DNA molecule. PIK3CA exon 9, PIK3CA exon 20, and KRAS exon 2 amplicons were amplified from normal lymphozyte DNA and quantified by a Picogreen assay. Equal amounts of the individual PCR products were mixed, diluted, and used as templates for the emulsion PCR. To distinguish single-template beads from multi-template beads sequence-specific fluorescent probes were hybidized to the beads after the emulsion PCR.

As part of the optimization process required for the success of the experiments described below, we identified conditions that produced relatively uniform aqueous droplets within the water-in-oil emulsion used for BEAMing. Using compartments of average 3 microns, we determined the relationship between the concentration of DNA templates and the fraction of beads that were produced from single templates. When there were two or more DNA templates within an aqueous droplet, beads containing more than one homogeneous DNA sequence were produced. With dilute DNA samples, very few beads would be expected to contain any DNA template, and most beads would therefore be "negative", i.e., not be extended. As shown in FIG. 7, increasing DNA concentrations resulted in progressively greater fractions of multi-template beads, as expected. The fraction of single-template beads was maximal at ~30 pg of template per emulsion PCR. At this concentration, 12% of the beads were single template, 9% were double-template, and the remaining 79% of the beads were negative. In subsequent experiments, we therefore used 20 to 40 pg of template DNA per reaction.

Figure 8B:
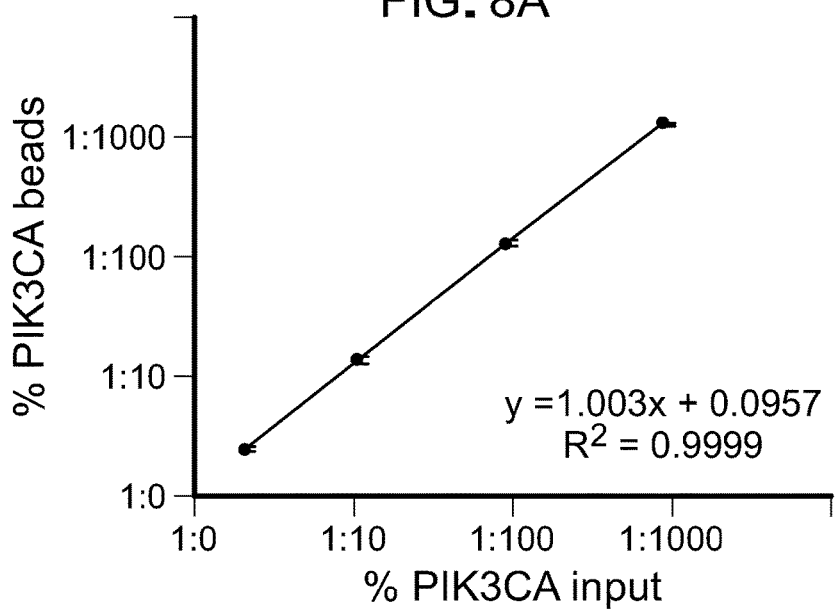
Figure 8C:
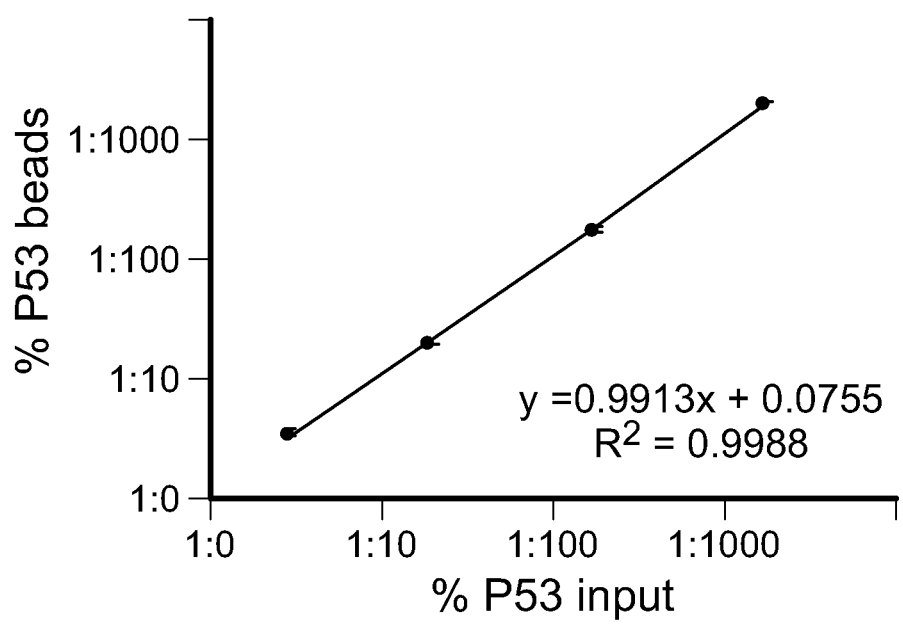

Another way to assess the quality of the beads produced by BEAMing and their single-template nature was through mixing experiments. For this purpose, templates containing KRAS2 and PIK3CA templates were mixed at various ratios and the proportion of beads containing either KRAS22 or PIK3CA extensions was measured by flow cytometry following BEAMing. If single templates were sufficient to generate robust PCR extension products on beads, then there should be a linear relationship between the ratio of input molecules and the ratio of beads containing one or the other type of template. Conversely, if more than one template molecule was required for extension on beads, or if a large fraction of aqueous compartments contained more than one template molecule, then this ratio would be skewed. For example, when the proportion of PIK3CA template molecules was low, there would be very few beads that contained a PIK3CA extension product that did not also contain a KRAS2 extension product. As shown in FIGS. 8a and 8b, the results of this mixing experiment clearly demonstrated a linear relationship between input template ratio and bead proportions generated, even at ratios as low as 1:1000 (R2=0.999, Slope=1.0). A similar linear relationship was found when an independent experiment was performed using a mixture of p53 and KRAS2 templates (FIG. 8C, R2=0.998, Slope=1.0).

Example 8

Rolling Circle Amplification on Beads Produced by BEAMing

Figure 6:
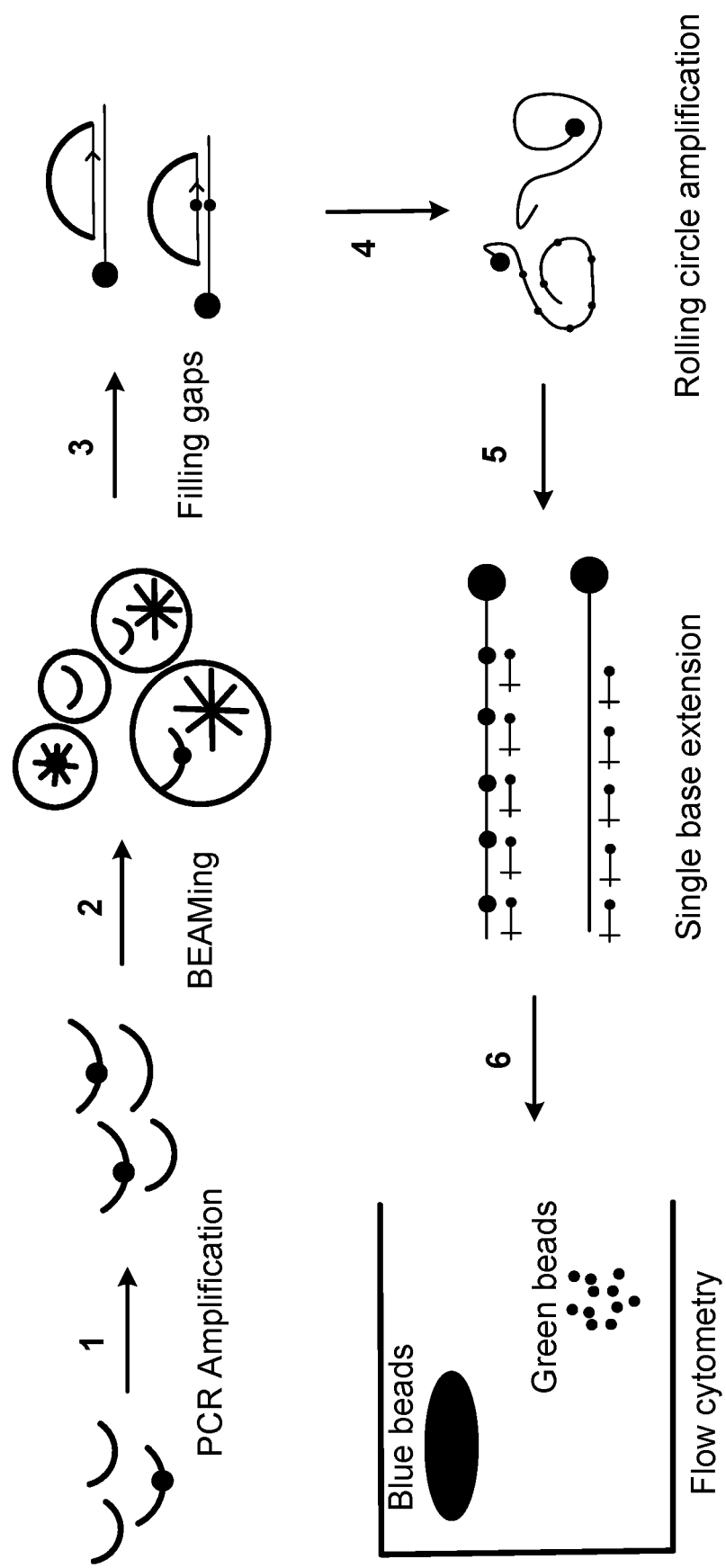
FIG. 6: Schematic of "BEAMing Up" assay
Figure 9A:
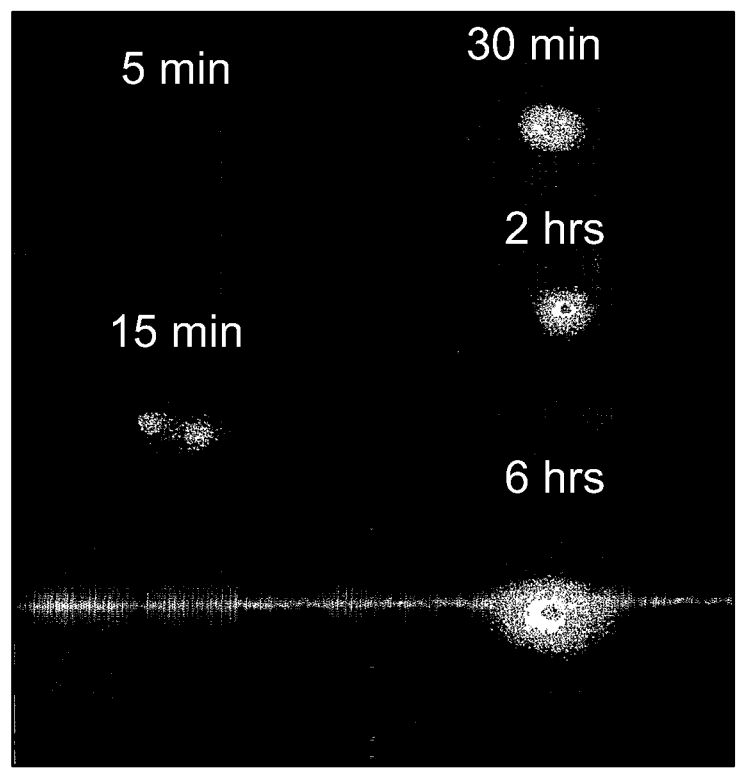
FIGS. 9A-9B: Rolling circle amplification (RCA) on beads.

To increase the amount of extended DNA on the beads, we investigated a variety of approaches to rolling circle amplification using extended PCR products on beads as templates. The most successful of these procedures is schematically shown in FIG. 6 detailed in the Methods section. A padlock or circularizable probe, with ends complementary to two non-adjacent sequences on the beads, was first annealed to the bead-bound DNA. The 0-30 bp intervening sequence was then filled in with a polymerase and the ends ligated. Because the 3' end of the PCR product attached to the beads was close to the padlocked oligo (9), the 3' end could be used as primer in a rolling circle amplification with φ29 polymerase. Rolling circle amplification continued linearly for at least 6 hours, and the DNA attached to the beads could be easily visualized in a fluorescence microscope following hybridization with sequence-specific FAM probe (FIG. 9a). If any of the enzymatic steps shown in FIG. 9a were eliminated, no increased signals on beads was observed (data not shown).

Figure 9B:
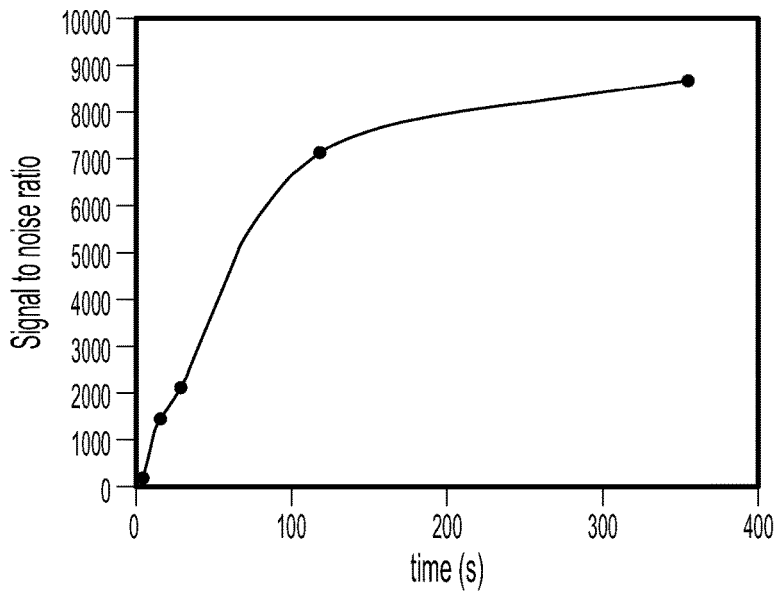

In addition to the increased signal per bead shown in FIG. 9a, the signal to noise ratio obtained upon analysis of beads was also increased. To assess the SNR, we used a fluorescein-labeled oligonucleotide complementary to the original PCR product strand attached to the beads. After hybridization to the original beads produced by BEAMing, the average signal intensity was 25-fold higher than that observed on beads that had been produced by BEAMing with an unrelated template, yielding a SNR of 25:1. Following RCA, the SNR increased to more than 9000-fold (FIG. 9b). Based on the relative signals obtained, we estimated that the length of DNA strands attached to the beads had increased from 100 bases to 40,000 bases by RCA. The reason for the SNR increase is because the background fluorescence signal following hybridization to beads without a complementary PCR product is due to autofluorescence plus non-specific binding of the probe to the beads. This background fluorescence signal is not increased much by RCA, while the specific hybridization signal is dramatically increased.

Figure 10A:
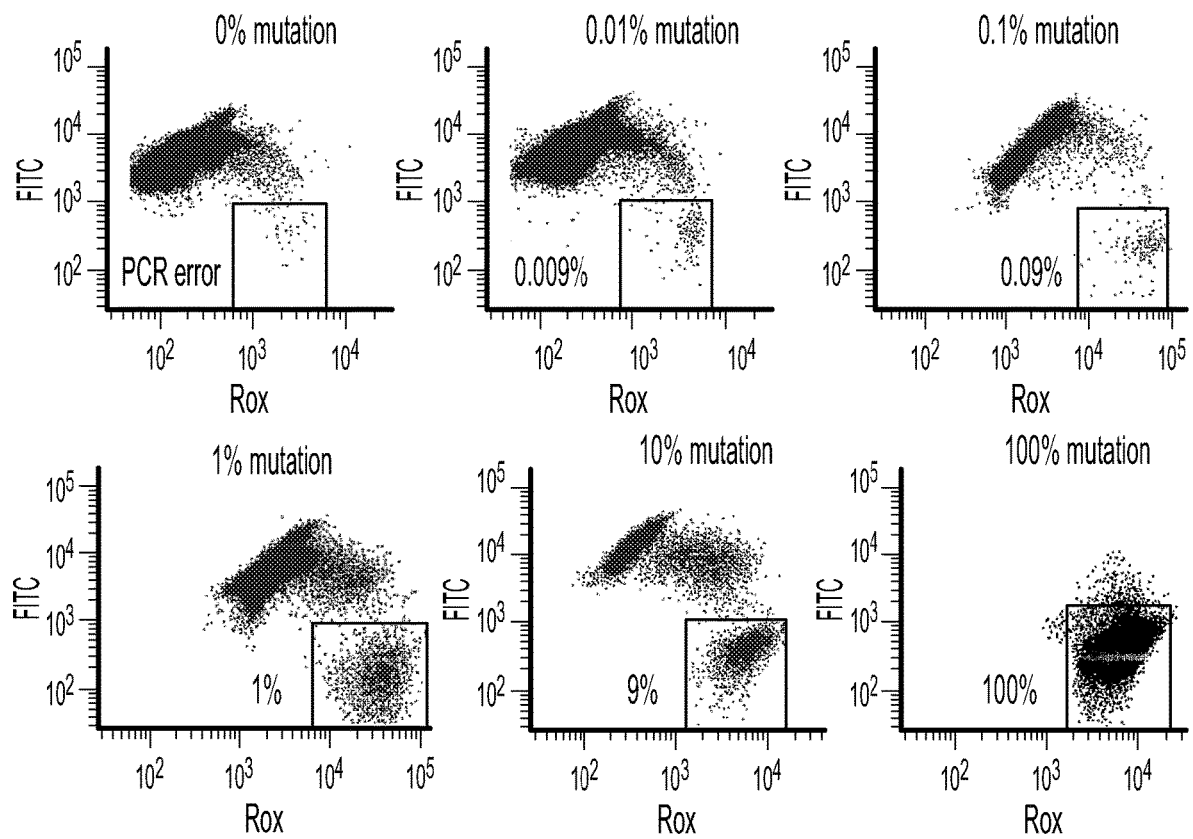
FIGS. 10A-10E: "BEAMing Up" for quantification of mutations in the presence of excessive amount of wild-type DNA.
Figure 10B:
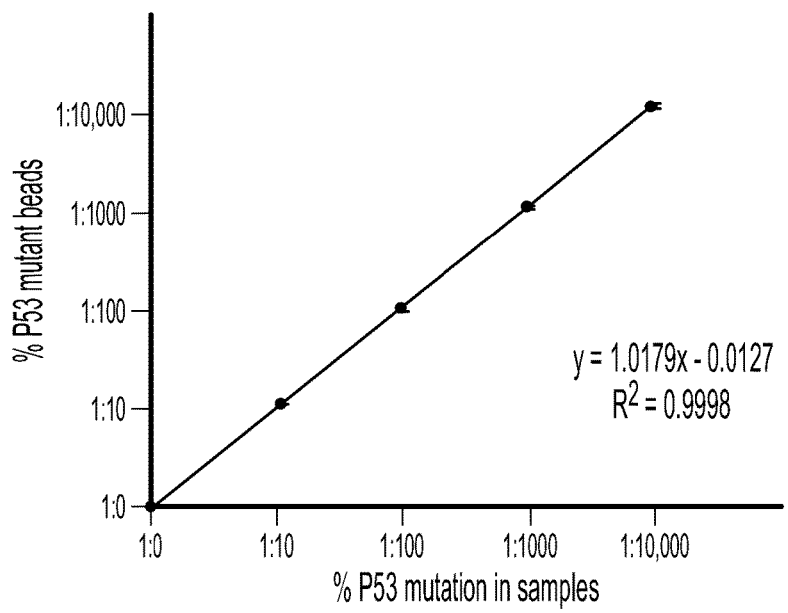
Figure 10C:
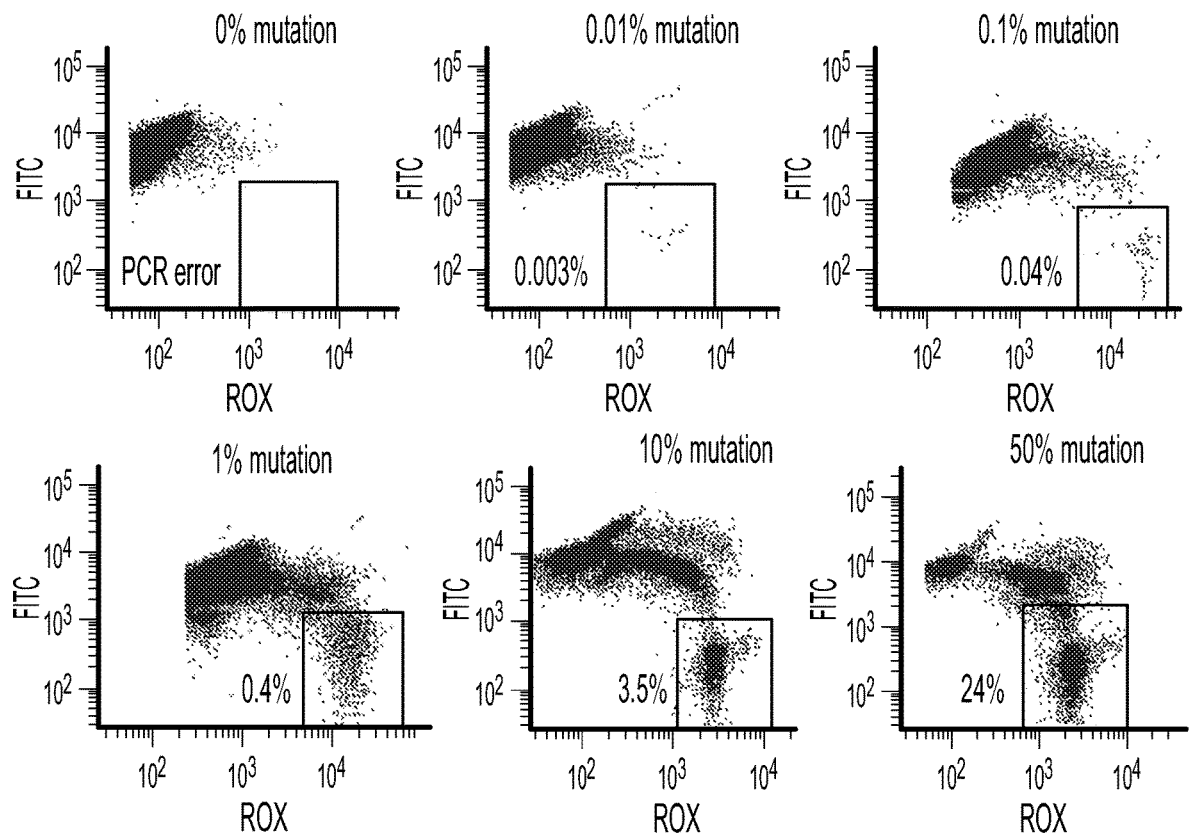
Figure 10D:
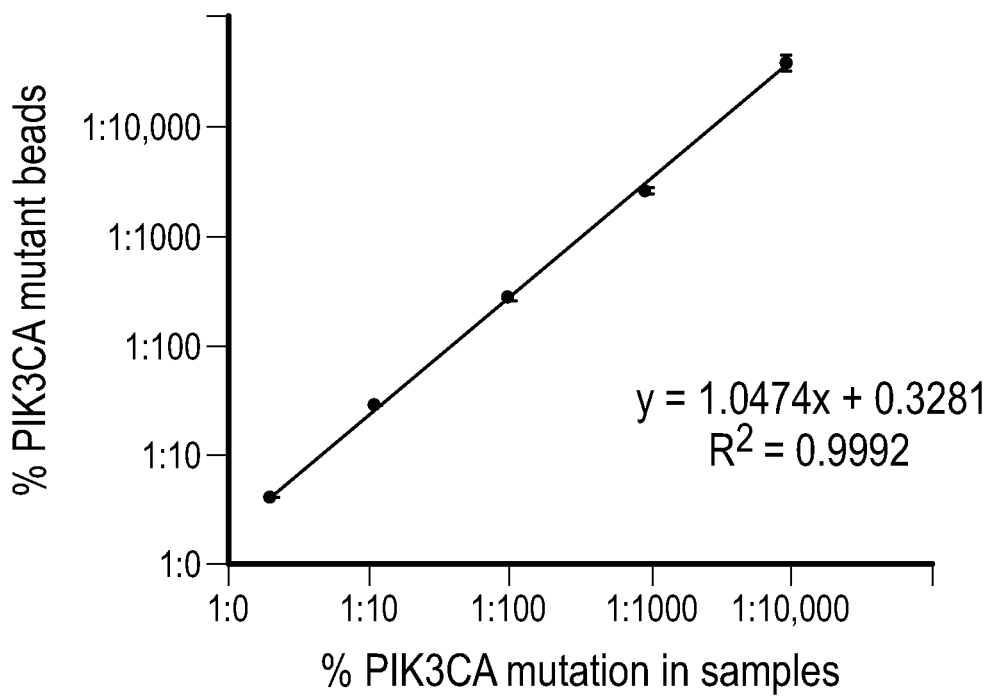
Figure 10E:
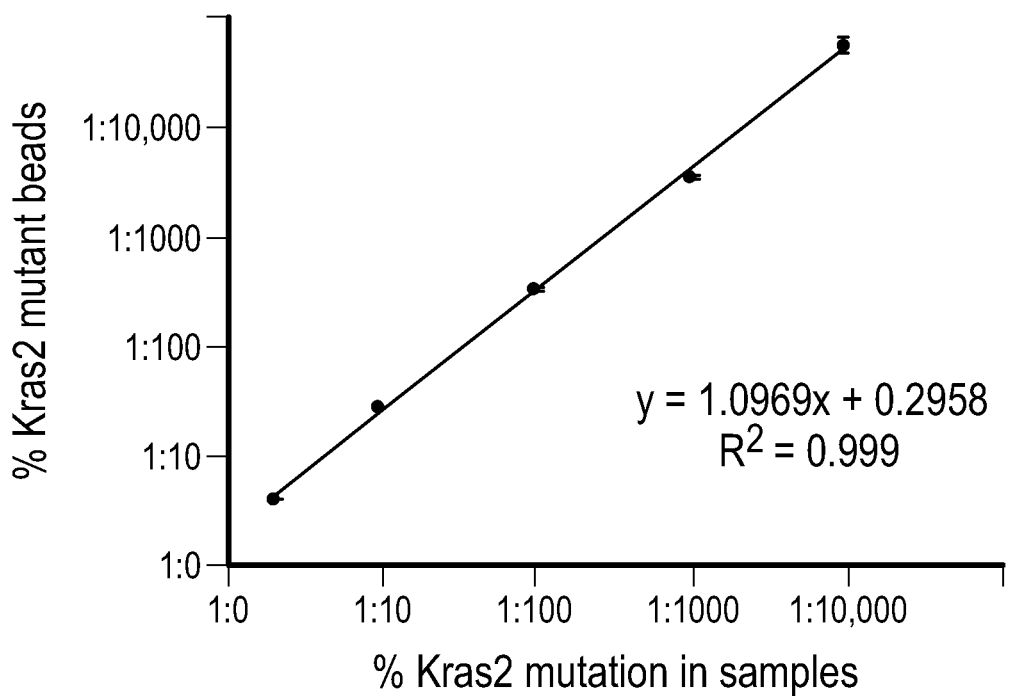

To ensure that the amplification procedure described in FIG. 9 (henceforth termed BEAMing Up) faithfully copied the sequences present on the original beads, we performed emulsion PCR using templates representing mixtures of wt and mutant DNA p53 sequences. The mutations were located in a region of the PCR product that was filled in by polymerase after annealing to the circularizable probe (FIG. 6). Flow cytometric data from this experiment are shown in FIG. 10a and graphed in FIG. 10b. From these data, it is clear that the fraction of beads containing mutant p53 sequences was proportional to the fraction of mutant p53 template molecules used for BEAMing. This was true over a very broad range of input fractions (R2=0.9998, slope=1.0). Similarly linear relationships between input fractions and bead fractions were found with independent emulsion PCR/RCA experiments using mutants of PIK3CA and KRAS (FIG. 10c, d, e).

Example 9

Error Rates of Polymerases Commonly Used for PCR

Examination of FIG. 10a shows that there were some beads that contained homogeneous mutant p53 sequences even when the template used to produce them was normal human genomic DNA (panel showing 0% mutations). These apparent mutations were caused by errors during the initial PCR used to generate the templates for BEAMing. PCR errors introduced during the emulsion PCR or RCA steps would not result in "mutant" beads, as such beads would be classified as multi-template beads and therefore not included in the analysis. However, errors during the initial PCR used to generate templates would be indistinguishable from mutations occurring in vivo: droplets containing such single mutant molecules would give rise to beads containing homogeneous mutant sequences. Accordingly, we suspected that the procedures described here could be used to directly assess the error rates of polymerases commonly used for PCR.

To determine error rates, we amplified exon 20 of the PIK3CA gene from genomic DNA from a normal individual with four different polymerases representing each of the major classes commercially available: Platinum Taq (Invitrogen), Platinum Taq High Fidelity (Invitrogen), PfuUltra Hotstart (Stratagene), and Phusion (NEB) DNA polymerase. Mutiple PCR reations were carried out according to manufacturers' recommendations. Thirty cycles were performed with each polymerase and real-time PCR showed that the PCR products were still increasing exponentially at this time point. Equivalent amounts of DNA were produced from each polymerase under the conditions used, and 20 pg of DNA was used for each BEAMing Up reaction.

Figure 11A:
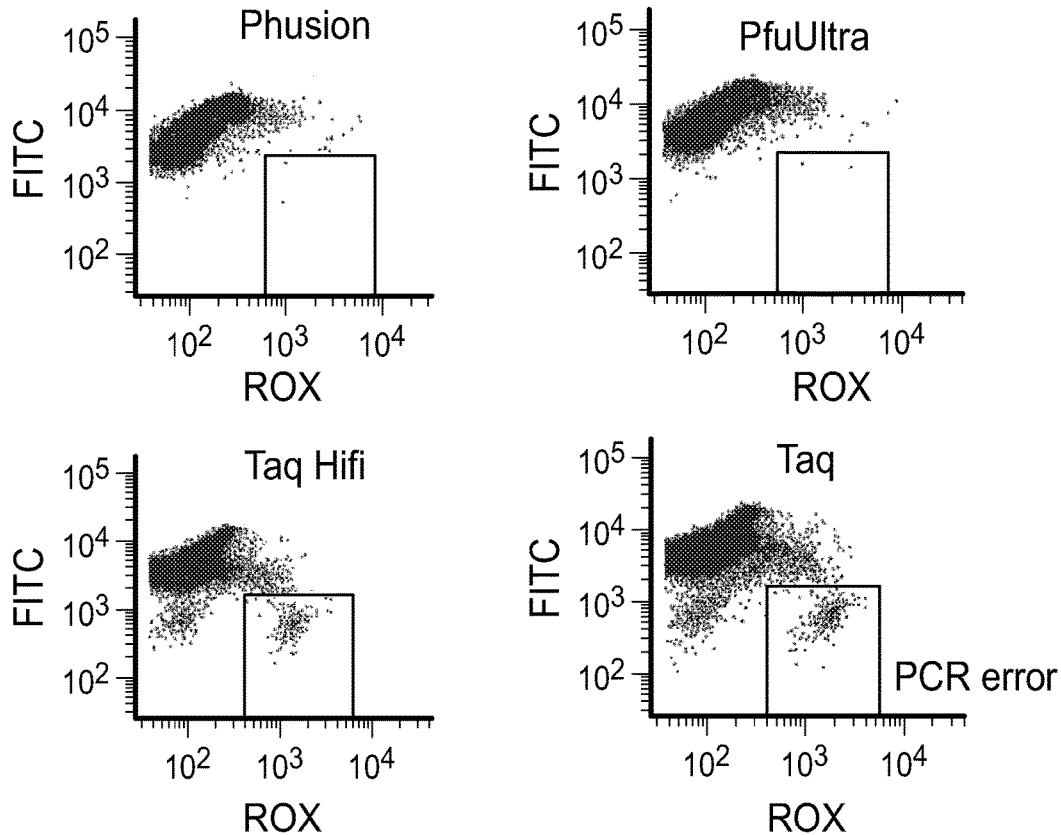
FIGS. 11A-11C: Quantification of error rates of commonly used polymerases for PCR.
Figure 11B:
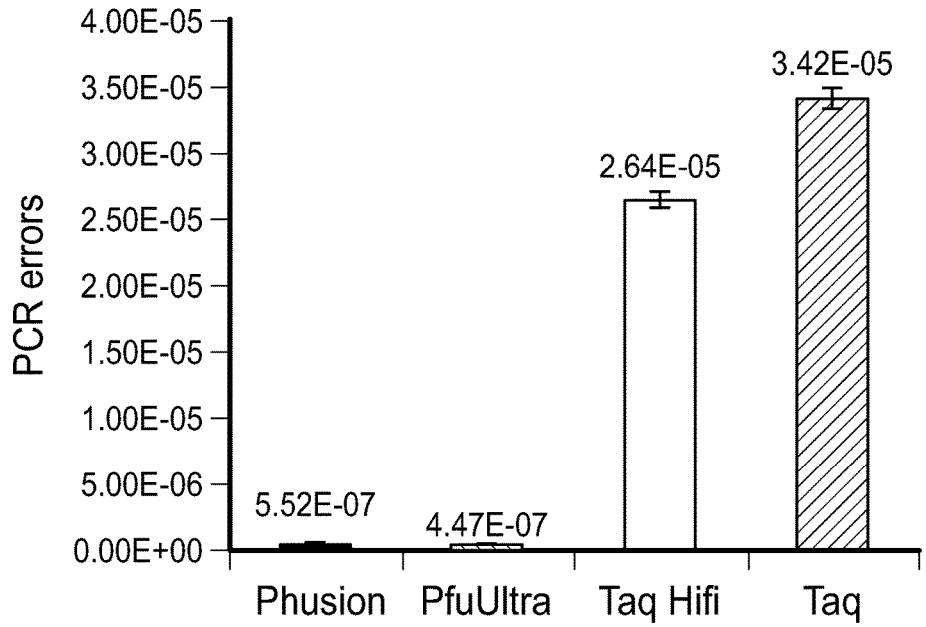
Figure 11C:
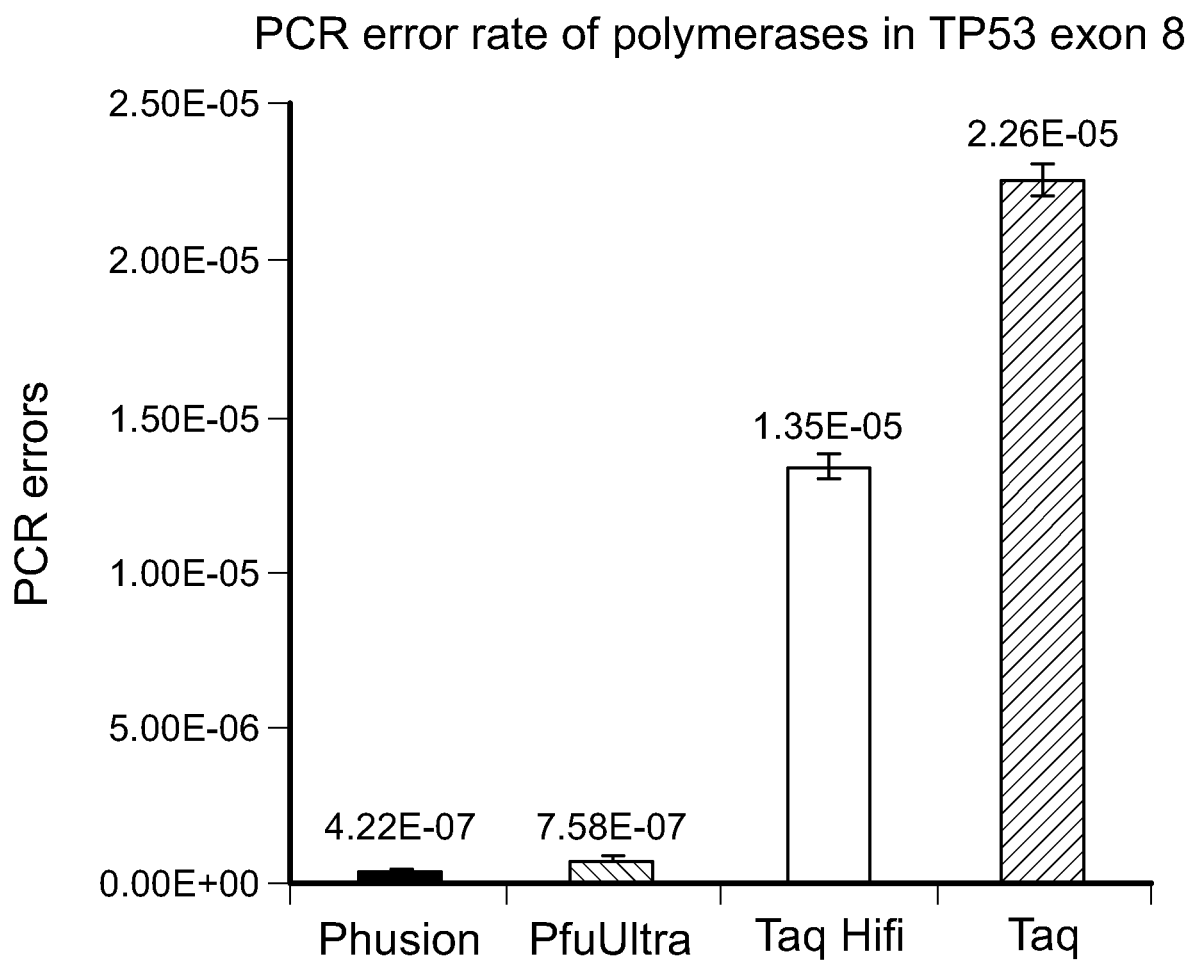

The results of these comparisons are shown in the flow cytometric profiles illustrated in FIG. 11a and statistically graphed in FIG. 11b. Taq had the highest error rate (3.4×10-5 errors per bp per cycle) and the error rate of Taq High Fidelity was just slightly less (FIG. 11b). In contrast, PfuUltra and Phusion polymerases had dramatically lower error rates (4.5 and 5.5×10$^{-7}$, respectively). Comparison of the errors generated through amplification of a completely different genomic DNA sequence (p53 exon 8) revealed qualitatively similar results (FIG. 11C). Through the absolute error rates with all four enzymes were slightly lower than found with the PIK3CA exon 20 amplicon, the relative error rates of Phusion and PfuUltra were at least 18-fold lower than the other two enzymes with both amplicons.

REFERENCES

The disclosure of each reference cited is expressly incorporated herein.

References

1. Vogelstein, B. & Kinzler, K. W. (2004) *Nat Med* 10, 789-99.
2. Smith, R. A., Cokkinides, V. & Eyre, H. J. (2005) *CA Cancer J Clin* 55, 31-44; quiz 55-6.
3. Breen, N. & Meissner, H. I. (2005) *Annu Rev Public Health* 26, 561-82.
4. Ransohoff, D. F. (2005) *Nat Rev Cancer* 5, 142-9.
5. Kaplan, R. M. (2005) *Recent Results Cancer Res* 166, 315-34.
6. Sidransky, D. (2002) *Nat Rev Cancer* 2, 210-9.
7. Verma, M. & Srivastava, S. (2003) *Recent Results Cancer Res* 163, 72-84; discussion 264-6.
8. Jaffer, F. A. & Weissleder, R. (2005) *Jama* 293, 855-62.
9. Sidransky, D., Von Eschenbach, A., Tsai, Y. C., Jones, P., Summerhayes, I., Marshall, F., Paul, M., Green, P., Hamilton, S. R., Frost, P. & et al. (1991) *Science* 252, 706-9.
10. Sidransky, D., Tokino, T., Hamilton, S. R., Kinzler, K. W., Levin, B., Frost, P. & Vogelstein, B. (1992) *Science* 256, 102-5.
11. Burchill, S. A. & Selby, P. J. (2000) *J Pathol* 190, 6-14.
12. Goessl, C. (2003) *Expert Rev Mol Diagn* 3, 431-42.
13. Lotze, M. T., Wang, E., *Marincola*, F. M., Hanna, N., Bugelski, P. J., Burns, C. A., Coukos, G., Damle, N., Godfrey, T. E., Howell, W. M., Panelli, M. C., Perricone, M. A., Petricoin, E. F., Sauter, G., Scheibenbogen, C., Shivers, S. C., Taylor, D. L., Weinstein, J. N. & Whiteside, T. L. (2005) *J Immunother* 28, 79-119.
14. Bremnes, R. M., Sirera, R. & Camps, C. (2005) *Lung Cancer* 49, 1-12.
15. Muller, H. M. & Widschwendter, M. (2003) *Expert Rev Mol Diagn* 3, 443-58.
16. Dressman, D., Yan, H., Traverso, G., Kinzler, K. W. & Vogelstein. B. (2003) *Proc Natl Acad Sci USA* 100, 8817-22.
17. Ghadessy, F. J. & Holliger, P. (2004) *Protein Eng Des Sel* 17, 201-4.
18. Bernath, K., Hai, M., Mastrobattista, E., Griffiths, A. D., Magdassi, S. & Tawfik, D. S. (2004) *Anal Biochem* 325, 151-7.
19. Leon, S. A., Shapiro, B., Sklaroff, D. M. & Yaros, M. J. (1977) *Cancer Res* 37, 646-50.
20. Sozzi, G., Conte, D., Mariani, L., Lo Vullo, S., Roz, L., Lombardo. C., Pierotti, M. A. & Tavecchio, L. (2001) *Cancer Res* 61, 4675-8.
21. Giacona, M. B., Ruben, G. C., Iczkowski, K. A., Roos, T. B., Porter, D. M. & Sorenson, G. D. (1998) *Pancreas* 17, 89-97.
22. Jahr, S., Hentze, H., Englisch, S., Hardt, D., Fackelmayer, F. O., Hesch, R. D. & Knippers, R. (2001) *Cancer Res* 61, 1659-65.
23. Kinzler, K. W. & Vogelstein, B. (1996) *Cell* 87, 159-170.
24. Yu, R. Z., Geary, R. S., Monteith, D. K., Matson, J., Truong, L., Fitchett, J. & Levin, A. A. (2004) *J Pharm Sci* 93, 48-59.
25. Lo, Y. M., Zhang, J., Leung, T. N., Lau, T. K., Chang, A. M. & Hjelm, N. M. (1999) *Am J Hum Genet* 64, 218-24.
26. Thomlinson, R. H. & Gray, L. H. (1955) *Br J Cancer* 9, 539-49.
27. Cerar, A., Zidar, N. & Vodopivec, B. (2004) *Pathol Res Pract* 200, 657-62.
28. Chen, S., Yu, L., Jiang, C., Zhao, Y., Sun, D., Li, S., Liao, G., Chen, Y., Fu, Q., Tao, Q., Ye, D., Hu, P., Khawli, L. A., Taylor, C. R., Epstein, A. L. & Ju, D. W. (2005) *J Clin Oncol* 23, 1538-47.
29. Leek, R. D., Landers, R. J., Harris, A. L. & Lewis, C. E. (1999) *Br J Cancer* 79, 991-5.
30. Choi, J. J., Reich, C. F., 3rd & Pisetsky, D. S. (2005) *Immunology* 115, 55-62.
31. Meyerhardt, J. A. & Mayer, R. J. (2005) *N Engl J Med* 352, 476-87.
32. Winawer, S., Faivre, J., Selby, J., Bertaro, L., Chen, T. H., Kroborg, O., Levin, B., Mandel, J., O'Morain, C., Richards, M., Rennert, G., Russo, A., Saito, H., Semigfnovsky, B., Wong, B. & Smith, R. (2005) *Ann Oncol* 16, 31-3.
33. Lieberman, D. A. & Atkin, W. (2004) *Aliment Pharmacol Ther* 19 Suppl 1, 71-6.
34. Ahlquist, D. A. & Shuber, A. P. (2002) *Clin Chim Acta* 315, 157-68.

References for Examples 5-9

1. Shendure J et al. Accurate Multiplex Polony Sequencing of an Evolved Bacterial Genome. *Science.* 5741, 1728-1732 (2005).
2. Margulies M et al. Genome sequencing in microfabricated high-density picolitre reactors. *Nature.* 437, 376-380 (2005).
3. Khrapko K et al. Mitochondrial mutational spectra in human cells and tissues. *Proc. Natl. Acad. Sci.* 94, 13798-13803 (1997).
4. Andre P, Kim A, Khrapko K & Thilly W G, Fidelity and mutational spectrum of Pfu DNA polymerase on a human mitochondrial DNA sequence. *Genome Res.* 7, 843-852 (1997).
5. Muniappan B P & Thilly W G. The DNA Polymerase β Replication Error Spectrum in the Adenomatous Polyposis *Coli* Gene Contains Human Colon Tumor Mutational Hotspots. *Cancer Res.* 62, 3271-3275 (2002).
6. Nilsson M et al. Padlock probes: Circularizing oligonucleotides for localized DNA detection. *Science.* 265, 2085-2088 (1994).
7. Lizardi P M et al. Mutation detection and single-molecule counting using isothermal rolling-circle amplification. *Nat Genet.* 19,225-232 (1998).
8. Hardenbol P et al. *Multiplexed genotyping with sequence-tagged molecular inversion probes. Nat. Biotechnol.* 21, 673-678 (2003).
9. Larsson C et al. In situ genotyping individual DNA molecules by target-primed rolling-circle amplification of padlock probes. *Nature Meth.* 1, 227-232 (2004).

TABLE 1

Primer sequences used for fragment sizing

| Patient No. | Use | Target region, nt | Size, bp | Forward primer, 5'-3' | Reverse primer, 5'- 3' |
|---|---|---|---|---|---|
| 29 | 1st PCR | 3853-3952 | 100 | GATGAAATAGGATGTAATCAGACGAC | CTTCAGCTGACCTAGTTCCAATC |
|  |  | 3853-4006 | 154 | GATGAAATAGGATGTAATCAGACGAC | TGCTGGATTTGGTTCTAGGG |
|  |  | 3853-4049 | 195 | GATGAAATAGGATGTAATCAGACGAC | TTGTGCCTGGCTGATTCTG |
|  |  | 3853-4155 | 296 | GATGAAATAGGATGTAATCAGACGAC | GCTAAACATGAGTGGGGTCTC |
|  |  | 3853-4249 | 397 | GATGAAATAGGATGTAATCAGACGAC | TGCCACTTACCATTCCACTG |
|  |  | 3510-4805 | 1296 | ACGTCATGTGGATCAGCCTATTG | GGTAATTTTGAAGCAGTCTGGGC |
|  | 2nd PCR Sequencing | 3861-3952 | 92 | GGATGTAATCAGACGACACAGG CAGACGACACAGGAAGCAGAT | CTTCAGCTGACCTAGTTCCAATC |
| 30 | 1st PCR | 4002-4094 | 93 | CAGCAGACTGCAGGGTTCTAG | CCACTTTTGGAGGGAGATTTC |
|  |  | 4002-4146 | 145 | CAGCAGACTGCAGGGTTCTAG | ATGAGTGGGGTCTCCTGAAC |
|  |  | 4002-4206 | 205 | CAGCAGACTGCAGGGTrCTAG | CTGGCAATCGAACGACTCTC |
|  |  | 4002-4299 | 298 | CAGCAGACTGCAGGGTTCTAG | CTTGGTGGCATGGTTTGTC |
|  |  | 4002-4411 | 410 | CAGCAGACTGCAGGGTTCTAG | TGCAGCTTGCTTAGGTCCAC |
|  |  | 3510-4805 | 1296 | ACGTCATGTGGATCAGCCTATTG | GGTAATTTTGAAGCAGTCTGGGC |
|  | 2nd PCR Sequencing | 4010-4094 | 85 | TGCAGGGTTCTAGTTTATCTTCAG GGTTCTAGTTTATCTTCAGAATCAGC | CCACTTTTGGAGGGAGATTTC |
| 32 | 1st PCR | 4401-4501 | 99 | TAAGCAAGCTGCAGTAAATGC | AAAATCCATCTGGAGTACTTTCC |
|  |  | 4401-4544 | 142 | TAAGCAAGCTGCAGTAAATGC | ATGGCTCATCGAGGCTCAG |
|  |  | 4401-4687 | 286 | TAAGCAAGCTGCAGTAAATGC | GGTCCTTTTCAGAATCAATAGTTTT |
|  |  | 4401-4875 | 473 | TAAGCAAGCTGCAGTAAATGC | TGCAACCTGTTTTGTGATGG |
|  |  | 3510-4805 | 1296 | ACGTCATGTGGATCAGCCTATTG | GGTAATTTTGAAGCAGTCTGGGC |
|  | 2nd PCR Sequencing | 4413-4501 | 89 | GCAGTAAATGCTGCAGTTCAGAG TTCAGAGGGTCCAGGTTCTTC | AAAATCCATCTGGAGTACTTTCC |

TABLE 2

Primer sequences used for BEAMing

| Target region, nt | Size, bp |  | Real-time PCR primer, 5'-3' | Emulsion PCR primer, 5'-3' |
|---|---|---|---|---|
| 3791-3890 | 100 | FWD | TAGAAGATACTCCAATATGTTTTTCAAG | TCCAATATGTTTTTCAAGATGTAGTTC |
|  |  | REV | Tag-TCTGCTTCCTGTGTCGTCTG | TCCCGCGAAATTAATACGAC |
| 3853-3952 | 100 | FWD | Tag-GATGAAATAGGATGTAATCAGACGAC | TCCCGCGAAATTAATACGAC |
|  |  | REV | CtTCAGCTGACCTAGTTCCAATC | CTTCAGCTGACCTAGTTCCAATC |
| 3870-3977 | 108 | FWD | Tag-TCAGACGACACAGGAAGCAG | TTGCTCACAGGATCTTCAG |
|  |  | REV | ACTGCTGGAACTTCGCTCAC | TCCCGCGAAATTAATACGAC |
| 3952-4046 | 95 | FWD | GATCCTGTGAGCGAAGTTCC | AGCGAAGTTCCAGCAGTGTC |
|  |  | REV | Tag-TGCCTGGCTGATTCTGAAG | TCCCGCGAAATTAATACGAC |
| 4002-4094 | 93 | FWD | CAGCAGACTGCAGGGTTCTAG | TGCAGGGTTCTAGTTTATCTTCAG |
|  |  | REV | Tag-CCACTTTTGGAGGGAGATTTC | TCCCGCGAAATTAATACGAC |
| 4063-4155 | 93 | FWD | Tag-TCTTCAGGAGCGAAATCTCC | ATGAGTGGGGTCTCCTGAAC |
|  |  | REV | GCTAAACATGAGTGOGGTCTC | TCCCGCGAAATTAATACGAC |
| 4085-4189 | 104 | FWD | CCAAAAGTGGTGCTCAGACA | GCTCAGACACCCAAAAGTCC |
|  |  | REV | Tag-CAAAACTATCAAGTGAACTGACAGAAG | TCCCGCGAAATTAATAGGAC |
| 4137-4239 | 103 | FWD | Tag-GACCCCACTCATGTTTAGCAG | CCACTGCATGGTTCACTCTG |
|  |  | REV | CATTCCACTGCATGGTTCAC | TCCCGCGAAATTAATACGAC |
| 4153-4248 | 96 | FWD | AGATGTACTTCTGTCAGTTCACTTGAT | CTTCTGTCAGTTCACTTGATAGTTTTG |
|  |  | REV | Tag-GCCACTTACCATTCCACTGC | TCCCGCGAAATTAATACGAC |
| 4235-4332 | 98 | FWD | Tag-CCATGCAGTGGAATGGTAAG | AGGTGTTTTACTTCTGCTTGGTG |
|  |  | REV | GGTGGAGGTGTTTTACTTCTGC | TCCCGCGAAATTAATACGAC |
| 4225-4322 | 98 | FWD | CCATGCAGTGGAATGGTAAG | TGGCATTATAAGCCCCAGTG |
|  |  | REV | Tag-GGTGGAGGTGTTTTACTTCTGC | TCCCGCGAAATTAATACGAC |
| 4276-4380 | 105 | FWD | GCCCTGGACAAACCATGC | GACAAACCATGCCACCAAG |
|  |  | REV | Tag-AGCAGTAGGTGCTTTATTTTAGG | TCCCGCGAAATTAATACGAC |
| 4361-4455 | 95 | FWD | Tag-AAAATAAAGCACCTACTGCTGAAAAG | GGAAGAACCTGGACCCTCTG |
|  |  | REV | AGCATCTGGAAGAACCTGGAC | TCCCGCGAAATTAATACGAC |
| 4413-4514 | 102 | FWD | AGTAAATGCTGCAGTTCAGAGG | CTGCAGTTCAGAGGGTCCAG |
|  |  | REV | Tag-CTGGATGAACAAGAAAATCCATC | TCCCGCGAAATTAATACGAC |
| 4610-4710 | 101 | FWD | CAGAATCAGAGCAGCCTAAAGAA | GCAGCCTAAAGAATCAAATGAAA |
|  |  | REV | Tag-ATCATCATCTGAATCATCTAATAGGTC | TCCCGCGAAATTAATACGAC |

TABLE 3

Primer sequences used for single base extension

| Target region, nt | Patient No. | Single base extension primer, 5'-3' | normal base | mutant base |
|---|---|---|---|---|
| 3791-3890 | 3, 6 | ATGTAGTTCATTATCATCTTTGTCATCAGCTGAAGAT | G | T |
| 3853-3952 | 19 | GACCTAGTTCCAATCTTTTCTTTTATTTCTGCTATTT | G | A |
| 3870-3977 | 13, 29, 14, 18 | CACAGGATCTTCAGCTGACCTAGTTCCAATCTTTT | C | A |
| 3952-4046 | 24 | GCACCCTAGAACCAAATCCAGCAGACTG | C | T |
| 4002-4094 | 33 | ATCAGCCAGGCACAAAGCTGTTGAATTTT | C | T |
|  | 30 | CAGCCAGGCACAAAGCTGTTGAATTTTCTT | C | A |
|  | 5 | CAGCCAGGCACAAAGCTGTTGAATTTTCTT | C | G |
| 4063-4155 | 23, 25 | CATAGTGTTCAGGTGGACTTTTGGGTGTCT | G | A |
| 4085-4189 | 4 | TGAACACTATGTTCAGGAGACCCCACTCA | T | A |
|  | 31 | CAGGAGACCCCACTCATGTTTAGCAGATG | T | A |
| 4137-4239 | 12 | ACGGAGCTGGCAATCGAACGACTCT | C | A |
| 4153-4248 | 9 | GTCGTTCGATTGCCAGCTCCGTT | C | T |
| 4235-4332 | 27 | GGTTTGTCCAGGGCTATCTGGAAGATCAC | T | G |
| 4225-4322 | 2, 7 | CCAGTGATCTTCCAGATAGCCCTGGA | C | T |
| 4276-4380 | 22 | GCAGAAGTAAAACACCTCCACCACCTCCT | C | T |
|  | 8 | CACCACCTCCTCAAACAGCTCAAACC | A | T |
|  | 1, 21, 17, 11 | CCACCTCCTCAAACAGCTCAAACCAAG | C | T |
| 4361-4455 | 20 | TGCAGCATTTACTGCAGCTTGCTTAGGTC | C | A |
| 4413-4514 | 32 | GAGGGTCCAGGTTCTTCCAGATGCTGATACTTTATTA | C | T |
|  | 15, 26 | CCAGGTTCTTCCAGATGCTGATACTTTATTACATTT | T | G |
|  | 16 | CAGATGCTGATACTTTATTACATTTTGCCACAGAA | A | G |
| 4610-4710 | 28, 10 | CAAATGAAAACCAAGAGAAAGAGGCAGAAAAAA | C | A |

TABLE 4

Quantification of APC Mutations in Plasma

| No. | Sex/Age (Yr) | Site | Dukes' Stage (TNM-Stage) | Diameter of lesion (cm) | Mutation identified in primary tumor (codon) | Fragments/ml plasma | # Fragments analysed | % Mutant fragments |
|---|---|---|---|---|---|---|---|---|
| 1 | M/50 | Ascending colon | Adenoma | 3.0 | C4348T(1450) | 2600 | 2350 | 0.002% |
| 2 | M/67 | Descending colon | Adenoma | 2.5 | C4285T (1429) | 5080 | 5080 | 0.001% |
| 3 | M/54 | Rectum | Adenoma | 4.0 | G3856T (1286) | 4150 | 4150 | 0.002% |
| 4 | F/82 | Rectum | Adenoma | 3.0 | 4147-4148InsA (1383) | 1350 | 1350 | 0.001% |
| 5 | F/65 | Rectum | Adenoma | 1.0 | C4067G (1356) | 42G0 | 4260 | 0.001% |
| 6 | F/71 | Ascending colon | Adenoma | 4.0 | C3856T (1286) | 4150 | 4150 | 0.001% |
| 7 | M/68 | Cecum | Adenoma | 6.5 | C4285T (1429) | 4760 | 4760 | 0.003% |
| 8 | M/93 | Ascending colon | Adenoma | 0.8 | A4345T (1449) | 4320 | 4320 | 0.001% |
| 9 | F/78 | Ascending colon | Adenoma | 30 | C4216T (1408) | 28570 | 28570 | 0.001% |
| 10 | F/59 | Sigmoid colon | Adenoma | 5.0 | 4666-4667InsA(1544) | 2160 | 2160 | 0.002% |
| 11 | F/73 | Ascending colon | Adenoma | 5.0 | C4348T (1460) | 8000 | 8000 | 0.02% |
|  |  |  | Median/Mean Mutant plasma samples per samples analysed |  |  | 4300/6300 |  | 0.02% 1/11 (9%) |
| 12 | F/81 | Sigmoid colon | A (T2N0M0) | 4.0 | G4189T (1397) | 7900 | 12000 | 0.01% |
| 13 | F/75 | Sigmoid colon | A (T2N0M0) | 2.5 | 3927-3931delAAAGA (1309) | 2160 | 2160 | 0.001% |
| 14 | M/60 | Sigmoid colon | A (T2N0M0) | 3.0 | 3927-3931delAAAGA (1309) | 4600 | 6900 | 0.04% |
| 15 | M/79 | Right colic flexure | A (T2N0M0) | 3.0 | 4470delT (1490) | 4600 | 3696 | 0.03% |
| 16 | M/70 | Ileocecal | A (T2N0M0) | 2.5 | 4481delA (1494) | 6200 | 3105 | 0.07% |
| 17 | F/68 | Ascending colon | A (T2N0M0) | 3.5 | C4348T (1450) | 2170 | 2170 | 0.001% |
| 18 | F/66 | Sigmoid colon | A (T2N0M0) | 2.5 | 3927-3931delAAAGA (1309) | 1920 | 1920 | 0.001% |
| 19 | M/66 | Rectum | A (T2N0M0) | 5.5 | G3907T (1303) | 2300 | 1170 | 0.12% |
|  |  |  | Median/Mean Mutant plasma samples per samples analysed |  |  | 3500/4000 |  | 0.04%/0.04% 5/8 (63%) |
| 20 | F/65 | Cecum | B (T3N0M0) | 3.5 | G4398T (1466) | 5300 | 5300 | 0.002% |
| 21 | M/71 | Sigmoid colon | B (T3N0M0) | 3.0 | C4348T (1450) | 2100 | 1863 | 0.19% |
| 22 | M/37 | Descending colon | B (T3N0M0) | 10.0 | C4330T (1444) | 5400 | 4887 | 1.28% |
| 23 | M/64 | Sigmoid colon | B (T3N0M0) | 6.5 | C4099T (1367) | 3810 | 3810 | 0.001% |
| 24 | M/72 | Sigmoid colon | B (T3N0M0) | 3.0 | C4012T (1338) | 4800 | 4800 | 0.03% |
| 25 | F/82 | Hepatic flexure | B (T3N0M0) | 4.0 | C4099T (1367) | 3840 | 3840 | 1.46% |
| 26 | M/83 | Ascending colon | B (T3N0M0) | 6.0 | 4470delT (1490) | 1600 | 1404 | 1.76% |
| 27 | M/61 | Sigmoid colon | B (T3N0M0) | 4.0 | 4260-4261delCA (1420) | 4200 | 4200 | 0.001% |

TABLE 4-continued

Quantification of APC Mutations in Plasma

| No. | Sex/Age (Yr) | Site | Dukes' Stage (TNM-Stage) | Diameter of lesion (cm) | Mutation identified in primary tumor (codon) | Fragments/ml plasma | # Fragments analysed | % Mutant fragments |
|---|---|---|---|---|---|---|---|---|
| | | | | | Median/Mean Mutant plasma samples per samples analysed | 4000/3900 | | 1.28%/0.94% 5/8 (63%) |
| 28 | F/83 | Ascending colon | D (T3N2M1) | 6.0 | 4666-4667InsA (1544) | 230000 | 24857 | 5.6% |
| 29 | M/55 | Sigmoid colon | D (T3N0M1) | 3.0 | G3925T (1309) | 69600 | 1636 | 27.4% |
| 30 | F/33 | Descending colon | D (T4N1M1) | 5.0 | C4067A (1356) | 18000 | 491 | 10.5% |
| 31 | M/64 | Sigmoid colon | D (T4N2M1) | 6.0 | T4161A (1387) | 26000 | 975 | 1.9% |
| 32 | M/66 | Rectum | D (T3N2M1) | 3.0 | 4468-4469delCA (1490) | 103200 | 1187 | 18.9% |
| 33 | F/60 | Rectum | D (T3N2M1) | 4.0 | 4059-4060InsT (1354) | 8400 | 850 | 2.0% |
| | | | | | Median/Mean Mutant plasma samples per samples analysed | | | 8.05%11/05%* 6/6 (100%) |

*Calculated only for samples in which mutuant frequency was significantly higher than in control samples, i.e., >0.003%.

TABLE 5

Mutant genomic sequences analyzed

| Source of genomic DNA | Amino acid change | Nucleotide change |
|---|---|---|
| Colon cancer cell line Co3 | Tp53 exon 8 H273R | CGT to CAT |
| Colon cancer cell line Co38 | PIK3CA exon 20 H1047R | CAT to CGT |
| Colon cancer cell line Co4 | KRAS2 exon 2 G12D | GGT to GAT |

TABLE 6

Primers used for analysis of p53

| | |
|---|---|
| Tp53 1st PCR forward primer | 5'-ATCCTGAGTAGTGGTAATCTACTGG-3' |
| Tp53 1st PCR reverse primer | 5'-TCCCGCGAAATTAATACGACTTGCGGAGATTCTCTTCCTC-3' |
| Tp53 emulsion PCR forward primer. | 5'TGGTAATCTACTGGGACGGAAC-3' |
| Tp53 padlock probe | 5'-Phosphate-GTGTTTGTGCCTGTCTTCCTTTTACGACGG CTCTGCCTCCTGCCTGCTTCTTCGTGCCTC GTTCTCGTGTAGACTGGGACGGAACAGC-3' |
| Tp53 hybridization probe | 5'-FAM-GCT TTG AGG TGC GTG TTT GTGCC-3' |
| Tp53 SBE primer | 5'-Cy5-CCCGAACA GCTTTGAGGT GC-3' |

TABLE 7

Primers used for analysis of PIK3CA

| | |
|---|---|
| PIK3CA exon 20 1st PCR forward primer | 5'-TCCCGCGAAATTAATACGACGCCTTAG ATAAAACTGAGCAAGAG-3' |
| PIK3CA exon 20 1st PCR reverse primer | 5'-GGAAGATCCAATCCATTTTTG-3' |
| PIK3CA exon 20 emulsion PCR reverse primer | 5'-CAATCCATTTTTGTTGTCCAG-3' |
| PIK3CA exon 20 padlock probe | 5'-Phosphate-ATTTGTTCATGAAATACTTCCTTTTACG ACGGCTCTGCCTCCTGCCTGCTTCTT GTGCCTCGTTCTCGTGTAGATTGTTGTC CAGCCAC-3' |
| PIK3CA exon 20 hybridization primer | 5'-FAM- TTG TTG TCC AGC CAC CAT GA-3' |
| PIK3CA exon 20 SBE primer | 5'-Cy5- TTG TTG TCC AGC CAC CAT GA-3' |
| PIK3CA exon 9 1st PCR forward primer | 5'-TCCCGCGAAATTAATACGACTGACAAA GAACAGCTCAAAGC-3' |
| PIK3CA exon 9 1st PCR reverse primer | 5'-TCCATTTTAGCACTTACCTGTGAC-3' |
| PIK3CA exon 9 emulsion PCR reverse primer | 5'-CTTACCTGTGACTCCATAGAAAATC-3' |
| PIK3CA exon 9 hybridization primer | 5'-Biotin-CCTGTGACTCCATAGAAAATCTTTCTCC TGCT-3' |

TABLE 8

Primers used for analysis of KRAS2

| | |
|---|---|
| KRAS2 exon 2 1st PCR forward primer | 5'-TCCCGCGAAATTAATACGACTGACTGAATATAAACTTGTGGTAGTTG-3' |
| KRAS2 exon 2 1st PCR reverse primer | 5'-CATATTCGTCCACAAAATGATTC-3' |
| KRAS2 exon 2 emulsion PCR reversed primer | 5'-AATGATTCTGAATTAGCTGTATCGTC-3' |

TABLE 8-continued

Primers used for analysis of KRAS2

| | |
|---|---|
| KRAS2 exon 2 padlock probe | 5'-Phosphate-GCTCCAACTACCACATTCCTTTTACGACGGCTCTGCCTCCTGCCTGCTCTTCGTGCTCTCGTTCTCGTGTAGACGGCACTCTTGCCTAC-3' |
| KRAS2 exon 2 SBE primer | 5'-Cy5- GGC ACT CTT GCC TAC GCC AC-3' |

We claim:

1. A method for detecting rare DNA mutations in a sample, comprising:
   performing real-time PCR on a sample using a high fidelity DNA polymerase to form a set of first amplicons;
   forming a water-in-oil microemulsion, comprising an aqueous phase and an oil phase, wherein the microemulsion comprises the set of first amplicons and beads, wherein the beads are bound to a plurality of molecules of a primer for amplifying the set of first amplicons;
   amplifying the set of first amplicons in the water-in-oil microemulsion, whereby product beads are formed which are bound to a set of second amplicons;
   separating the aqueous phase from the oil phase of the microemulsion;
   breaking the microemulsion;
   associating a nucleotide of a wild-type gene from the set of second amplicons with a fluorescently-labelled tag and associating at least one nucleotide of a genetic mutation from the set of second amplicons with a different fluorescently-labelled tag; and
   analyzing single beads to the exclusion of bead doublets and bead aggregates, wherein single beads are analyzed by flow cytometry to measure the signal associated with individual beads, thereby detecting rare DNA mutations in a sample.

2. The method of claim 1, wherein the sample is obtained from blood, urine, or stool.

3. The method of claim 1, wherein the sample is obtained from plasma.

4. The method of claim 1, the microemulsion are formed with a tissue homogenizer.

5. The method of claim 1, wherein the microemulsion are formed with a mechanical tissue homogenizer.

6. The method of claim 1, wherein the microemulsion are formed with a rotor-stator tissue homogenizer.

7. The method of claim 1, wherein two high fidelity polymerases are used in parallel and compared to ascertain relative fidelity.

8. The method of claim 1, wherein the microemulsion comprise a thermostable emulsifying agent.

9. The method of claim 1, wherein the associating step comprises single base extension.

10. The method of claim 1, wherein the associating step comprises sequencing by synthesis.

11. The method of claim 1, wherein the method detects at least 0.2% mutant DNA fragments within the sample.

* * * * *

SEQUENCE LISTING

<160> NUMBER OF SEQ ID NOS: 154

<210> SEQ ID NO 1
<211> LENGTH: 26
<212> TYPE: DNA
<213> ORGANISM: Artificial Sequence
<220> FEATURE:
<223> OTHER INFORMATION: primer or probe

<400> SEQUENCE: 1
gatgaaatag gatgtaatca gacgac                                          26

<210> SEQ ID NO 2
<211> LENGTH: 26
<212> TYPE: DNA
<213> ORGANISM: Artificial Sequence
<220> FEATURE:
<223> OTHER INFORMATION: primer or probe

<400> SEQUENCE: 2
gatgaaatag gatgtaatca gacgac                                          26

<210> SEQ ID NO 3
<211> LENGTH: 26
<212> TYPE: DNA
<213> ORGANISM: Artificial Sequence
<220> FEATURE:
<223> OTHER INFORMATION: primer or probe

<400> SEQUENCE: 3
gatgaaatag gatgtaatca gacgac                                          26

<210> SEQ ID NO 4
<211> LENGTH: 26
<212> TYPE: DNA
<213> ORGANISM: Artificial Sequence
<220> FEATURE:
<223> OTHER INFORMATION: primer or probe

<400> SEQUENCE: 4
gatgaaatag gatgtaatca gacgac                                          26

<210> SEQ ID NO 5
<211> LENGTH: 26
<212> TYPE: DNA
<213> ORGANISM: Artificial Sequence
<220> FEATURE:
<223> OTHER INFORMATION: primer or probe

<400> SEQUENCE: 5
gatgaaatag gatgtaatca gacgac                                          26

<210> SEQ ID NO 6

```
<211> LENGTH: 23
<212> TYPE: DNA
<213> ORGANISM: Artificial Sequence
<220> FEATURE:
<223> OTHER INFORMATION: primer or probe

<400> SEQUENCE: 6
acgtcatgtg gatcagccta ttg                                              23

<210> SEQ ID NO 7
<211> LENGTH: 22
<212> TYPE: DNA
<213> ORGANISM: Artificial Sequence
<220> FEATURE:
<223> OTHER INFORMATION: primer or probe

<400> SEQUENCE: 7
ggatgtaatc agacgacaca gg                                               22

<210> SEQ ID NO 8
<211> LENGTH: 21
<212> TYPE: DNA
<213> ORGANISM: Artificial Sequence
<220> FEATURE:
<223> OTHER INFORMATION: primer or probe

<400> SEQUENCE: 8
cagacgacac aggaagcaga t                                                21

<210> SEQ ID NO 9
<211> LENGTH: 21
<212> TYPE: DNA
<213> ORGANISM: Artificial Sequence
<220> FEATURE:
<223> OTHER INFORMATION: primer or probe

<400> SEQUENCE: 9
cagcagactg cagggttcta g                                                21

<210> SEQ ID NO 10
<211> LENGTH: 21
<212> TYPE: DNA
<213> ORGANISM: Artificial Sequence
<220> FEATURE:
<223> OTHER INFORMATION: primer or probe

<400> SEQUENCE: 10
cagcagactg cagggttcta g                                                21

<210> SEQ ID NO 11
<211> LENGTH: 21
<212> TYPE: DNA
<213> ORGANISM: Artificial Sequence
<220> FEATURE:
<223> OTHER INFORMATION: primer or probe

<400> SEQUENCE: 11
cagcagactg cagggttcta g                                                21

<210> SEQ ID NO 12
<211> LENGTH: 21
<212> TYPE: DNA
<213> ORGANISM: Artificial Sequence
<220> FEATURE:
<223> OTHER INFORMATION: primer or probe

<400> SEQUENCE: 12
```

-continued

```
cagcagactg cagggttcta g                                              21

<210> SEQ ID NO 13
<211> LENGTH: 21
<212> TYPE: DNA
<213> ORGANISM: Artificial Sequence
<220> FEATURE:
<223> OTHER INFORMATION: primer or probe

<400> SEQUENCE: 13
cagcagactg cagggttcta g                                              21

<210> SEQ ID NO 14
<211> LENGTH: 23
<212> TYPE: DNA
<213> ORGANISM: Artificial Sequence
<220> FEATURE:
<223> OTHER INFORMATION: primer or probe

<400> SEQUENCE: 14
acgtcatgtg gatcagccta ttg                                            23

<210> SEQ ID NO 15
<211> LENGTH: 24
<212> TYPE: DNA
<213> ORGANISM: Artificial Sequence
<220> FEATURE:
<223> OTHER INFORMATION: primer or probe

<400> SEQUENCE: 15
tgcagggttc tagtttatct tcag                                           24

<210> SEQ ID NO 16
<211> LENGTH: 26
<212> TYPE: DNA
<213> ORGANISM: Artificial Sequence
<220> FEATURE:
<223> OTHER INFORMATION: primer or probe

<400> SEQUENCE: 16
ggttctagtt tatcttcaga atcagc                                         26

<210> SEQ ID NO 17
<211> LENGTH: 21
<212> TYPE: DNA
<213> ORGANISM: Artificial Sequence
<220> FEATURE:
<223> OTHER INFORMATION: primer or probe

<400> SEQUENCE: 17
taagcaagct gcagtaaatg c                                              21

<210> SEQ ID NO 18
<211> LENGTH: 21
<212> TYPE: DNA
<213> ORGANISM: Artificial Sequence
<220> FEATURE:
<223> OTHER INFORMATION: primer or probe

<400> SEQUENCE: 18
taagcaagct gcagtaaatg c                                              21

<210> SEQ ID NO 19
<211> LENGTH: 21
<212> TYPE: DNA
```

```
<213> ORGANISM: Artificial Sequence
<220> FEATURE:
<223> OTHER INFORMATION: primer or probe

<400> SEQUENCE: 19
taagcaagct gcagtaaatg c                                              21

<210> SEQ ID NO 20
<211> LENGTH: 21
<212> TYPE: DNA
<213> ORGANISM: Artificial Sequence
<220> FEATURE:
<223> OTHER INFORMATION: primer or probe

<400> SEQUENCE: 20
taagcaagct gcagtaaatg c                                              21

<210> SEQ ID NO 21
<211> LENGTH: 23
<212> TYPE: DNA
<213> ORGANISM: Artificial Sequence
<220> FEATURE:
<223> OTHER INFORMATION: primer or probe

<400> SEQUENCE: 21
acgtcatgtg gatcagccta ttg                                            23

<210> SEQ ID NO 22
<211> LENGTH: 23
<212> TYPE: DNA
<213> ORGANISM: Artificial Sequence
<220> FEATURE:
<223> OTHER INFORMATION: primer or probe

<400> SEQUENCE: 22
gcagtaaatg ctgcagttca gag                                            23

<210> SEQ ID NO 23
<211> LENGTH: 21
<212> TYPE: DNA
<213> ORGANISM: Artificial Sequence
<220> FEATURE:
<223> OTHER INFORMATION: primer or probe

<400> SEQUENCE: 23
ttcagagggt ccaggttctt c                                              21

<210> SEQ ID NO 24
<211> LENGTH: 23
<212> TYPE: DNA
<213> ORGANISM: Artificial Sequence
<220> FEATURE:
<223> OTHER INFORMATION: primer or probe

<400> SEQUENCE: 24
cttcagctga cctagttcca atc                                            23

<210> SEQ ID NO 25
<211> LENGTH: 20
<212> TYPE: DNA
<213> ORGANISM: Artificial Sequence
<220> FEATURE:
<223> OTHER INFORMATION: primer or probe

<400> SEQUENCE: 25
tgctggattt ggttctaggg                                                20
```

<210> SEQ ID NO 26
<211> LENGTH: 19
<212> TYPE: DNA
<213> ORGANISM: Artificial Sequence
<220> FEATURE:
<223> OTHER INFORMATION: primer or probe

<400> SEQUENCE: 26
ttgtgcctgg ctgattctg                                            19

<210> SEQ ID NO 27
<211> LENGTH: 21
<212> TYPE: DNA
<213> ORGANISM: Artificial Sequence
<220> FEATURE:
<223> OTHER INFORMATION: primer or probe

<400> SEQUENCE: 27
gctaaacatg agtggggtct c                                         21

<210> SEQ ID NO 28
<211> LENGTH: 20
<212> TYPE: DNA
<213> ORGANISM: Artificial Sequence
<220> FEATURE:
<223> OTHER INFORMATION: primer or probe

<400> SEQUENCE: 28
tgccacttac cattccactg                                           20

<210> SEQ ID NO 29
<211> LENGTH: 23
<212> TYPE: DNA
<213> ORGANISM: Artificial Sequence
<220> FEATURE:
<223> OTHER INFORMATION: primer or probe

<400> SEQUENCE: 29
ggtaattttg aagcagtctg ggc                                       23

<210> SEQ ID NO 30
<211> LENGTH: 23
<212> TYPE: DNA
<213> ORGANISM: Artificial Sequence
<220> FEATURE:
<223> OTHER INFORMATION: primer or probe

<400> SEQUENCE: 30
cttcagctga cctagttcca atc                                       23

<210> SEQ ID NO 31
<211> LENGTH: 21
<212> TYPE: DNA
<213> ORGANISM: Artificial Sequence
<220> FEATURE:
<223> OTHER INFORMATION: primer or probe

<400> SEQUENCE: 31
ccacttttgg agggagattt c                                         21

<210> SEQ ID NO 32
<211> LENGTH: 20
<212> TYPE: DNA
<213> ORGANISM: Artificial Sequence
<220> FEATURE:

<223> OTHER INFORMATION: primer or probe

<400> SEQUENCE: 32
atgagtgggg tctcctgaac                                              20

<210> SEQ ID NO 33
<211> LENGTH: 20
<212> TYPE: DNA
<213> ORGANISM: Artificial Sequence
<220> FEATURE:
<223> OTHER INFORMATION: primer or probe

<400> SEQUENCE: 33
ctggcaatcg aacgactctc                                              20

<210> SEQ ID NO 34
<211> LENGTH: 19
<212> TYPE: DNA
<213> ORGANISM: Artificial Sequence
<220> FEATURE:
<223> OTHER INFORMATION: primer or probe

<400> SEQUENCE: 34
cttggtggca tggtttgtc                                               19

<210> SEQ ID NO 35
<211> LENGTH: 20
<212> TYPE: DNA
<213> ORGANISM: Artificial Sequence
<220> FEATURE:
<223> OTHER INFORMATION: primer or probe

<400> SEQUENCE: 35
tgcagcttgc ttaggtccac                                              20

<210> SEQ ID NO 36
<211> LENGTH: 23
<212> TYPE: DNA
<213> ORGANISM: Artificial Sequence
<220> FEATURE:
<223> OTHER INFORMATION: primer or probe

<400> SEQUENCE: 36
ggtaattttg aagcagtctg ggc                                          23

<210> SEQ ID NO 37
<211> LENGTH: 21
<212> TYPE: DNA
<213> ORGANISM: Artificial Sequence
<220> FEATURE:
<223> OTHER INFORMATION: primer or probe

<400> SEQUENCE: 37
ccacttttgg agggagattt c                                            21

<210> SEQ ID NO 38
<211> LENGTH: 23
<212> TYPE: DNA
<213> ORGANISM: Artificial Sequence
<220> FEATURE:
<223> OTHER INFORMATION: primer or probe

<400> SEQUENCE: 38
aaaatccatc tggagtactt tcc                                          23

<210> SEQ ID NO 39
<211> LENGTH: 19
<212> TYPE: DNA
<213> ORGANISM: Artificial Sequence
<220> FEATURE:
<223> OTHER INFORMATION: primer or probe

<400> SEQUENCE: 39
atggctcatc gaggctcag                                            19

<210> SEQ ID NO 40
<211> LENGTH: 25
<212> TYPE: DNA
<213> ORGANISM: Artificial Sequence
<220> FEATURE:
<223> OTHER INFORMATION: primer or probe

<400> SEQUENCE: 40
ggtccttttc agaatcaata gtttt                                     25

<210> SEQ ID NO 41
<211> LENGTH: 20
<212> TYPE: DNA
<213> ORGANISM: Artificial Sequence
<220> FEATURE:
<223> OTHER INFORMATION: primer or probe

<400> SEQUENCE: 41
tgcaacctgt tttgtgatgg                                           20

<210> SEQ ID NO 42
<211> LENGTH: 23
<212> TYPE: DNA
<213> ORGANISM: Artificial Sequence
<220> FEATURE:
<223> OTHER INFORMATION: primer or probe

<400> SEQUENCE: 42
ggtaattttg aagcagtctg ggc                                       23

<210> SEQ ID NO 43
<211> LENGTH: 23
<212> TYPE: DNA
<213> ORGANISM: Artificial Sequence
<220> FEATURE:
<223> OTHER INFORMATION: primer or probe

<400> SEQUENCE: 43
aaaatccatc tggagtactt tcc                                       23

<210> SEQ ID NO 44
<211> LENGTH: 28
<212> TYPE: DNA
<213> ORGANISM: Artificial Sequence
<220> FEATURE:
<223> OTHER INFORMATION: primer or probe

<400> SEQUENCE: 44
tagaagatac tccaatatgt ttttcaag                                  28

<210> SEQ ID NO 45
<211> LENGTH: 20
<212> TYPE: DNA
<213> ORGANISM: Artificial Sequence
<220> FEATURE:
<223> OTHER INFORMATION: primer or probe

```
<400> SEQUENCE: 45
tctgcttcct gtgtcgtctg                                              20

<210> SEQ ID NO 46
<211> LENGTH: 26
<212> TYPE: DNA
<213> ORGANISM: Artificial Sequence
<220> FEATURE:
<223> OTHER INFORMATION: primer or probe

<400> SEQUENCE: 46
gatgaaatag gatgtaatca gacgac                                       26

<210> SEQ ID NO 47
<211> LENGTH: 23
<212> TYPE: DNA
<213> ORGANISM: Artificial Sequence
<220> FEATURE:
<223> OTHER INFORMATION: primer or probe

<400> SEQUENCE: 47
cttcagctga cctagttcca atc                                          23

<210> SEQ ID NO 48
<211> LENGTH: 20
<212> TYPE: DNA
<213> ORGANISM: Artificial Sequence
<220> FEATURE:
<223> OTHER INFORMATION: primer or probe

<400> SEQUENCE: 48
tcagacgaca caggaagcag                                              20

<210> SEQ ID NO 49
<211> LENGTH: 20
<212> TYPE: DNA
<213> ORGANISM: Artificial Sequence
<220> FEATURE:
<223> OTHER INFORMATION: primer or probe

<400> SEQUENCE: 49
actgctggaa cttcgctcac                                              20

<210> SEQ ID NO 50
<211> LENGTH: 20
<212> TYPE: DNA
<213> ORGANISM: Artificial Sequence
<220> FEATURE:
<223> OTHER INFORMATION: primer or probe

<400> SEQUENCE: 50
gatcctgtga gcgaagttcc                                              20

<210> SEQ ID NO 51
<211> LENGTH: 19
<212> TYPE: DNA
<213> ORGANISM: Artificial Sequence
<220> FEATURE:
<223> OTHER INFORMATION: primer or probe

<400> SEQUENCE: 51
tgcctggctg attctgaag                                               19

<210> SEQ ID NO 52
<211> LENGTH: 21
```

<212> TYPE: DNA
<213> ORGANISM: Artificial Sequence
<220> FEATURE:
<223> OTHER INFORMATION: primer or probe

<400> SEQUENCE: 52
cagcagactg cagggttcta g                                    21

<210> SEQ ID NO 53
<211> LENGTH: 21
<212> TYPE: DNA
<213> ORGANISM: Artificial Sequence
<220> FEATURE:
<223> OTHER INFORMATION: primer or probe

<400> SEQUENCE: 53
ccactttkgg agggagattt c                                    21

<210> SEQ ID NO 54
<211> LENGTH: 20
<212> TYPE: DNA
<213> ORGANISM: Artificial Sequence
<220> FEATURE:
<223> OTHER INFORMATION: primer or probe

<400> SEQUENCE: 54
tcttcaggag cgaaatctcc                                      20

<210> SEQ ID NO 55
<211> LENGTH: 21
<212> TYPE: DNA
<213> ORGANISM: Artificial Sequence
<220> FEATURE:
<223> OTHER INFORMATION: primer or probe

<400> SEQUENCE: 55
gctaaacatg agtggggtct c                                    21

<210> SEQ ID NO 56
<211> LENGTH: 20
<212> TYPE: DNA
<213> ORGANISM: Artificial Sequence
<220> FEATURE:
<223> OTHER INFORMATION: primer or probe

<400> SEQUENCE: 56
ccaaaagtgg tgctcagaca                                      20

<210> SEQ ID NO 57
<211> LENGTH: 27
<212> TYPE: DNA
<213> ORGANISM: Artificial Sequence
<220> FEATURE:
<223> OTHER INFORMATION: primer or probe

<400> SEQUENCE: 57
caaaactatc aagtgaactg acagaag                              27

<210> SEQ ID NO 58
<211> LENGTH: 21
<212> TYPE: DNA
<213> ORGANISM: Artificial Sequence
<220> FEATURE:
<223> OTHER INFORMATION: primer or probe

<400> SEQUENCE: 58

```
gaccccactc atgtttagca g                                            21
```

<210> SEQ ID NO 59
<211> LENGTH: 20
<212> TYPE: DNA
<213> ORGANISM: Artificial Sequence
<220> FEATURE:
<223> OTHER INFORMATION: primer or probe

<400> SEQUENCE: 59

```
cattccactg catggttcac                                              20
```

<210> SEQ ID NO 60
<211> LENGTH: 27
<212> TYPE: DNA
<213> ORGANISM: Artificial Sequence
<220> FEATURE:
<223> OTHER INFORMATION: primer or probe

<400> SEQUENCE: 60

```
agatgtactt ctgtcagttc acttgat                                      27
```

<210> SEQ ID NO 61
<211> LENGTH: 20
<212> TYPE: DNA
<213> ORGANISM: Artificial Sequence
<220> FEATURE:
<223> OTHER INFORMATION: primer or probe

<400> SEQUENCE: 61

```
gccacttacc attccactgc                                              20
```

<210> SEQ ID NO 62
<211> LENGTH: 20
<212> TYPE: DNA
<213> ORGANISM: Artificial Sequence
<220> FEATURE:
<223> OTHER INFORMATION: primer or probe

<400> SEQUENCE: 62

```
ccatgcagtg gaatggtaag                                              20
```

<210> SEQ ID NO 63
<211> LENGTH: 22
<212> TYPE: DNA
<213> ORGANISM: Artificial Sequence
<220> FEATURE:
<223> OTHER INFORMATION: primer or probe

<400> SEQUENCE: 63

```
ggtggaggtg ttttacttct gc                                           22
```

<210> SEQ ID NO 64
<211> LENGTH: 20
<212> TYPE: DNA
<213> ORGANISM: Artificial Sequence
<220> FEATURE:
<223> OTHER INFORMATION: primer or probe

<400> SEQUENCE: 64

```
ccatgcagtg gaatggtaag                                              20
```

<210> SEQ ID NO 65
<211> LENGTH: 22
<212> TYPE: DNA
<213> ORGANISM: Artificial Sequence

```
<220> FEATURE:
<223> OTHER INFORMATION: primer or probe

<400> SEQUENCE: 65
ggtggaggtg ttttacttct gc                                              22

<210> SEQ ID NO 66
<211> LENGTH: 18
<212> TYPE: DNA
<213> ORGANISM: Artificial Sequence
<220> FEATURE:
<223> OTHER INFORMATION: primer or probe

<400> SEQUENCE: 66
gccctggaca aaccatgc                                                   18

<210> SEQ ID NO 67
<211> LENGTH: 24
<212> TYPE: DNA
<213> ORGANISM: Artificial Sequence
<220> FEATURE:
<223> OTHER INFORMATION: primer or probe

<400> SEQUENCE: 67
agcagtaggt gctttatttt tagg                                            24

<210> SEQ ID NO 68
<211> LENGTH: 26
<212> TYPE: DNA
<213> ORGANISM: Artificial Sequence
<220> FEATURE:
<223> OTHER INFORMATION: primer or probe

<400> SEQUENCE: 68
aaaataaagc acctactgct gaaaag                                          26

<210> SEQ ID NO 69
<211> LENGTH: 21
<212> TYPE: DNA
<213> ORGANISM: Artificial Sequence
<220> FEATURE:
<223> OTHER INFORMATION: primer or probe

<400> SEQUENCE: 69
agcatctgga agaacctgga c                                               21

<210> SEQ ID NO 70
<211> LENGTH: 22
<212> TYPE: DNA
<213> ORGANISM: Artificial Sequence
<220> FEATURE:
<223> OTHER INFORMATION: primer or probe

<400> SEQUENCE: 70
agtaaatgct gcagttcaga gg                                              22

<210> SEQ ID NO 71
<211> LENGTH: 23
<212> TYPE: DNA
<213> ORGANISM: Artificial Sequence
<220> FEATURE:
<223> OTHER INFORMATION: primer or probe

<400> SEQUENCE: 71
ctggatgaac aagaaaatcc atc                                             23
```

<210> SEQ ID NO 72
<211> LENGTH: 23
<212> TYPE: DNA
<213> ORGANISM: Artificial Sequence
<220> FEATURE:
<223> OTHER INFORMATION: primer or probe

<400> SEQUENCE: 72
cagaatcaga gcagcctaaa gaa                                              23

<210> SEQ ID NO 73
<211> LENGTH: 27
<212> TYPE: DNA
<213> ORGANISM: Artificial Sequence
<220> FEATURE:
<223> OTHER INFORMATION: primer or probe

<400> SEQUENCE: 73
atcatcatct gaatcatcta ataggtc                                          27

<210> SEQ ID NO 74
<211> LENGTH: 27
<212> TYPE: DNA
<213> ORGANISM: Artificial Sequence
<220> FEATURE:
<223> OTHER INFORMATION: primer or probe

<400> SEQUENCE: 74
tccaatatgt ttttcaagat gtagttc                                          27

<210> SEQ ID NO 75
<211> LENGTH: 20
<212> TYPE: DNA
<213> ORGANISM: Artificial Sequence
<220> FEATURE:
<223> OTHER INFORMATION: primer or probe

<400> SEQUENCE: 75
tcccgcgaaa ttaatacgac                                                  20

<210> SEQ ID NO 76
<211> LENGTH: 20
<212> TYPE: DNA
<213> ORGANISM: Artificial Sequence
<220> FEATURE:
<223> OTHER INFORMATION: primer or probe

<400> SEQUENCE: 76
tcccgcgaaa ttaatacgac                                                  20

<210> SEQ ID NO 77
<211> LENGTH: 23
<212> TYPE: DNA
<213> ORGANISM: Artificial Sequence
<220> FEATURE:
<223> OTHER INFORMATION: primer or probe

<400> SEQUENCE: 77
cttcagctga cctagttcca atc                                              23

<210> SEQ ID NO 78
<211> LENGTH: 20
<212> TYPE: DNA
<213> ORGANISM: Artificial Sequence
<220> FEATURE:
<223> OTHER INFORMATION: primer or probe

<400> SEQUENCE: 78
ttcgctcaca ggatcttcag                                              20

<210> SEQ ID NO 79
<211> LENGTH: 20
<212> TYPE: DNA
<213> ORGANISM: Artificial Sequence
<220> FEATURE:
<223> OTHER INFORMATION: primer or probe

<400> SEQUENCE: 79
tcccgcgaaa ttaatacgac                                              20

<210> SEQ ID NO 80
<211> LENGTH: 20
<212> TYPE: DNA
<213> ORGANISM: Artificial Sequence
<220> FEATURE:
<223> OTHER INFORMATION: primer or probe

<400> SEQUENCE: 80
agcgaagttc cagcagtgtc                                              20

<210> SEQ ID NO 81
<211> LENGTH: 20
<212> TYPE: DNA
<213> ORGANISM: Artificial Sequence
<220> FEATURE:
<223> OTHER INFORMATION: primer or probe

<400> SEQUENCE: 81
tcccgcgaaa ttaatacgac                                              20

<210> SEQ ID NO 82
<211> LENGTH: 24
<212> TYPE: DNA
<213> ORGANISM: Artificial Sequence
<220> FEATURE:
<223> OTHER INFORMATION: primer or probe

<400> SEQUENCE: 82
tgcagggttc tagtttatct tcag                                         24

<210> SEQ ID NO 83
<211> LENGTH: 20
<212> TYPE: DNA
<213> ORGANISM: Artificial Sequence
<220> FEATURE:
<223> OTHER INFORMATION: primer or probe

<400> SEQUENCE: 83
tcccgcgaaa ttaatacgac                                              20

<210> SEQ ID NO 84
<211> LENGTH: 20
<212> TYPE: DNA
<213> ORGANISM: Artificial Sequence
<220> FEATURE:
<223> OTHER INFORMATION: primer or probe

<400> SEQUENCE: 84
atgagtgggg tctcctgaac                                              20

<210> SEQ ID NO 85

```
<211> LENGTH: 20
<212> TYPE: DNA
<213> ORGANISM: Artificial Sequence
<220> FEATURE:
<223> OTHER INFORMATION: primer or probe

<400> SEQUENCE: 85
tcccgcgaaa ttaatacgac                                              20

<210> SEQ ID NO 86
<211> LENGTH: 20
<212> TYPE: DNA
<213> ORGANISM: Artificial Sequence
<220> FEATURE:
<223> OTHER INFORMATION: primer or probe

<400> SEQUENCE: 86
gctcagacac ccaaaagtcc                                              20

<210> SEQ ID NO 87
<211> LENGTH: 20
<212> TYPE: DNA
<213> ORGANISM: Artificial Sequence
<220> FEATURE:
<223> OTHER INFORMATION: primer or probe

<400> SEQUENCE: 87
tcccgcgaaa ttaatacgac                                              20

<210> SEQ ID NO 88
<211> LENGTH: 20
<212> TYPE: DNA
<213> ORGANISM: Artificial Sequence
<220> FEATURE:
<223> OTHER INFORMATION: primer or probe

<400> SEQUENCE: 88
ccactgcatg gttcactctg                                              20

<210> SEQ ID NO 89
<211> LENGTH: 20
<212> TYPE: DNA
<213> ORGANISM: Artificial Sequence
<220> FEATURE:
<223> OTHER INFORMATION: primer or probe

<400> SEQUENCE: 89
tcccgcgaaa ttaatacgac                                              20

<210> SEQ ID NO 90
<211> LENGTH: 27
<212> TYPE: DNA
<213> ORGANISM: Artificial Sequence
<220> FEATURE:
<223> OTHER INFORMATION: primer or probe

<400> SEQUENCE: 90
cttctgtcag ttcacttgat agttttg                                      27

<210> SEQ ID NO 91
<211> LENGTH: 20
<212> TYPE: DNA
<213> ORGANISM: Artificial Sequence
<220> FEATURE:
<223> OTHER INFORMATION: primer or probe

<400> SEQUENCE: 91
```
tcccgcgaaa ttaatacgac                                              20

<210> SEQ ID NO 92
<211> LENGTH: 23
<212> TYPE: DNA
<213> ORGANISM: Artificial Sequence
<220> FEATURE:
<223> OTHER INFORMATION: primer or probe

<400> SEQUENCE: 92
aggtgtttta cttctgcttg gtg                                          23

<210> SEQ ID NO 93
<211> LENGTH: 20
<212> TYPE: DNA
<213> ORGANISM: Artificial Sequence
<220> FEATURE:
<223> OTHER INFORMATION: primer or probe

<400> SEQUENCE: 93
tcccgcgaaa ttaatacgac                                              20

<210> SEQ ID NO 94
<211> LENGTH: 20
<212> TYPE: DNA
<213> ORGANISM: Artificial Sequence
<220> FEATURE:
<223> OTHER INFORMATION: primer or probe

<400> SEQUENCE: 94
tggcattata agccccagtg                                              20

<210> SEQ ID NO 95
<211> LENGTH: 20
<212> TYPE: DNA
<213> ORGANISM: Artificial Sequence
<220> FEATURE:
<223> OTHER INFORMATION: primer or probe

<400> SEQUENCE: 95
tcccgcgaaa ttaatacgac                                              20

<210> SEQ ID NO 96
<211> LENGTH: 19
<212> TYPE: DNA
<213> ORGANISM: Artificial Sequence
<220> FEATURE:
<223> OTHER INFORMATION: primer or probe

<400> SEQUENCE: 96
gacaaaccat gccaccaag                                               19

<210> SEQ ID NO 97
<211> LENGTH: 20
<212> TYPE: DNA
<213> ORGANISM: Artificial Sequence
<220> FEATURE:
<223> OTHER INFORMATION: primer or probe

<400> SEQUENCE: 97
tcccgcgaaa ttaatacgac                                              20

<210> SEQ ID NO 98
<211> LENGTH: 20
<212> TYPE: DNA

```
<213> ORGANISM: Artificial Sequence
<220> FEATURE:
<223> OTHER INFORMATION: primer or probe

<400> SEQUENCE: 98
ggaagaacct ggaccctctg                                               20

<210> SEQ ID NO 99
<211> LENGTH: 20
<212> TYPE: DNA
<213> ORGANISM: Artificial Sequence
<220> FEATURE:
<223> OTHER INFORMATION: primer or probe

<400> SEQUENCE: 99
tcccgcgaaa ttaatacgac                                               20

<210> SEQ ID NO 100
<211> LENGTH: 20
<212> TYPE: DNA
<213> ORGANISM: Artificial Sequence
<220> FEATURE:
<223> OTHER INFORMATION: primer or probe

<400> SEQUENCE: 100
ctgcagttca gagggtccag                                               20

<210> SEQ ID NO 101
<211> LENGTH: 20
<212> TYPE: DNA
<213> ORGANISM: Artificial Sequence
<220> FEATURE:
<223> OTHER INFORMATION: primer or probe

<400> SEQUENCE: 101
tcccgcgaaa ttaatacgac                                               20

<210> SEQ ID NO 102
<211> LENGTH: 23
<212> TYPE: DNA
<213> ORGANISM: Artificial Sequence
<220> FEATURE:
<223> OTHER INFORMATION: primer or probe

<400> SEQUENCE: 102
gcagcctaaa gaatcaaatg aaa                                           23

<210> SEQ ID NO 103
<211> LENGTH: 20
<212> TYPE: DNA
<213> ORGANISM: Artificial Sequence
<220> FEATURE:
<223> OTHER INFORMATION: primer or probe

<400> SEQUENCE: 103
tcccgcgaaa ttaatacgac                                               20

<210> SEQ ID NO 104
<211> LENGTH: 37
<212> TYPE: DNA
<213> ORGANISM: Artificial Sequence
<220> FEATURE:
<223> OTHER INFORMATION: primer or probe

<400> SEQUENCE: 104
atgtagttca ttatcatctt tgtcatcagc tgaagat                            37
```

```
<210> SEQ ID NO 105
<211> LENGTH: 37
<212> TYPE: DNA
<213> ORGANISM: Artificial Sequence
<220> FEATURE:
<223> OTHER INFORMATION: primer or probe

<400> SEQUENCE: 105
gacctagttc caatcttttc ttttatttct gctattt                                    37

<210> SEQ ID NO 106
<211> LENGTH: 35
<212> TYPE: DNA
<213> ORGANISM: Artificial Sequence
<220> FEATURE:
<223> OTHER INFORMATION: primer or probe

<400> SEQUENCE: 106
cacaggatct tcagctgacc tagttccaat ctttt                                      35

<210> SEQ ID NO 107
<211> LENGTH: 28
<212> TYPE: DNA
<213> ORGANISM: Artificial Sequence
<220> FEATURE:
<223> OTHER INFORMATION: primer or probe

<400> SEQUENCE: 107
gcaccctaga accaaatcca gcagactg                                              28

<210> SEQ ID NO 108
<211> LENGTH: 29
<212> TYPE: DNA
<213> ORGANISM: Artificial Sequence
<220> FEATURE:
<223> OTHER INFORMATION: primer or probe

<400> SEQUENCE: 108
atcagccagg cacaaagctg ttgaatttt                                             29

<210> SEQ ID NO 109
<211> LENGTH: 30
<212> TYPE: DNA
<213> ORGANISM: Artificial Sequence
<220> FEATURE:
<223> OTHER INFORMATION: primer or probe

<400> SEQUENCE: 109
cagccaggca caaagctgtt gaattttctt                                            30

<210> SEQ ID NO 110
<211> LENGTH: 30
<212> TYPE: DNA
<213> ORGANISM: Artificial Sequence
<220> FEATURE:
<223> OTHER INFORMATION: primer or probe

<400> SEQUENCE: 110
cagccaggca caaagctgtt gaattttctt                                            30

<210> SEQ ID NO 111
<211> LENGTH: 30
<212> TYPE: DNA
<213> ORGANISM: Artificial Sequence
<220> FEATURE:
```

<223> OTHER INFORMATION: primer or probe

<400> SEQUENCE: 111
catagtgttc aggtggactt ttgggtgtct                                            30

<210> SEQ ID NO 112
<211> LENGTH: 29
<212> TYPE: DNA
<213> ORGANISM: Artificial Sequence
<220> FEATURE:
<223> OTHER INFORMATION: primer or probe

<400> SEQUENCE: 112
tgaacactat gttcaggaga ccccactca                                             29

<210> SEQ ID NO 113
<211> LENGTH: 29
<212> TYPE: DNA
<213> ORGANISM: Artificial Sequence
<220> FEATURE:
<223> OTHER INFORMATION: primer or probe

<400> SEQUENCE: 113
caggagaccc cactcatgtt tagcagatg                                             29

<210> SEQ ID NO 114
<211> LENGTH: 25
<212> TYPE: DNA
<213> ORGANISM: Artificial Sequence
<220> FEATURE:
<223> OTHER INFORMATION: primer or probe

<400> SEQUENCE: 114
acggagctgg caatcgaacg actct                                                 25

<210> SEQ ID NO 115
<211> LENGTH: 23
<212> TYPE: DNA
<213> ORGANISM: Artificial Sequence
<220> FEATURE:
<223> OTHER INFORMATION: primer or probe

<400> SEQUENCE: 115
gtcgttcgat tgccagctcc gtt                                                   23

<210> SEQ ID NO 116
<211> LENGTH: 29
<212> TYPE: DNA
<213> ORGANISM: Artificial Sequence
<220> FEATURE:
<223> OTHER INFORMATION: primer or probe

<400> SEQUENCE: 116
ggtttgtcca gggctatctg gaagatcac                                             29

<210> SEQ ID NO 117
<211> LENGTH: 26
<212> TYPE: DNA
<213> ORGANISM: Artificial Sequence
<220> FEATURE:
<223> OTHER INFORMATION: primer or probe

<400> SEQUENCE: 117
ccagtgatct tccagatagc cctgga                                                26

```
<210> SEQ ID NO 118
<211> LENGTH: 29
<212> TYPE: DNA
<213> ORGANISM: Artificial Sequence
<220> FEATURE:
<223> OTHER INFORMATION: primer or probe

<400> SEQUENCE: 118
gcagaagtaa aacacctcca ccacctcct                                  29

<210> SEQ ID NO 119
<211> LENGTH: 26
<212> TYPE: DNA
<213> ORGANISM: Artificial Sequence
<220> FEATURE:
<223> OTHER INFORMATION: primer or probe

<400> SEQUENCE: 119
caccacctcc tcaaacagct caaacc                                     26

<210> SEQ ID NO 120
<211> LENGTH: 27
<212> TYPE: DNA
<213> ORGANISM: Artificial Sequence
<220> FEATURE:
<223> OTHER INFORMATION: primer or probe

<400> SEQUENCE: 120
ccacctcctc aaacagctca aaccaag                                    27

<210> SEQ ID NO 121
<211> LENGTH: 29
<212> TYPE: DNA
<213> ORGANISM: Artificial Sequence
<220> FEATURE:
<223> OTHER INFORMATION: primer or probe

<400> SEQUENCE: 121
tgcagcattt actgcagctt gcttaggtc                                  29

<210> SEQ ID NO 122
<211> LENGTH: 37
<212> TYPE: DNA
<213> ORGANISM: Artificial Sequence
<220> FEATURE:
<223> OTHER INFORMATION: primer or probe

<400> SEQUENCE: 122
gagggtccag gttcttccag atgctgatac tttatta                         37

<210> SEQ ID NO 123
<211> LENGTH: 36
<212> TYPE: DNA
<213> ORGANISM: Artificial Sequence
<220> FEATURE:
<223> OTHER INFORMATION: primer or probe

<400> SEQUENCE: 123
ccaggttctt ccagatgctg atactttatt acattt                          36

<210> SEQ ID NO 124
<211> LENGTH: 35
<212> TYPE: DNA
<213> ORGANISM: Artificial Sequence
<220> FEATURE:
<223> OTHER INFORMATION: primer or probe
```

```
<400> SEQUENCE: 124
cagatgctga tactttatta cattttgcca cagaa                                    35

<210> SEQ ID NO 125
<211> LENGTH: 33
<212> TYPE: DNA
<213> ORGANISM: Artificial Sequence
<220> FEATURE:
<223> OTHER INFORMATION: primer or probe

<400> SEQUENCE: 125
caaatgaaaa ccaagagaaa gaggcagaaa aaa                                      33

<210> SEQ ID NO 126
<211> LENGTH: 20
<212> TYPE: DNA
<213> ORGANISM: Artificial Sequence
<220> FEATURE:
<223> OTHER INFORMATION: primer or probe

<400> SEQUENCE: 126
tcccgcgaaa ttaatacgac                                                     20

<210> SEQ ID NO 127
<211> LENGTH: 20
<212> TYPE: DNA
<213> ORGANISM: Artificial Sequence
<220> FEATURE:
<223> OTHER INFORMATION: primer or probe

<400> SEQUENCE: 127
tcccgcgaaa ttaatacgac                                                     20

<210> SEQ ID NO 128
<211> LENGTH: 23
<212> TYPE: DNA
<213> ORGANISM: Artificial Sequence
<220> FEATURE:
<223> OTHER INFORMATION: primer or probe

<400> SEQUENCE: 128
acgtcatgtg gatcagccta ttg                                                 23

<210> SEQ ID NO 129
<211> LENGTH: 23
<212> TYPE: DNA
<213> ORGANISM: Artificial Sequence
<220> FEATURE:
<223> OTHER INFORMATION: primer or probe

<400> SEQUENCE: 129
ggtaattttg aagcagtctg ggc                                                 23

<210> SEQ ID NO 130
<211> LENGTH: 22
<212> TYPE: DNA
<213> ORGANISM: Artificial Sequence
<220> FEATURE:
<223> OTHER INFORMATION: primer or probe

<400> SEQUENCE: 130
tctggacaaa gcagtaaaac cg                                                  22

<210> SEQ ID NO 131
<211> LENGTH: 19
```

```
<212> TYPE: DNA
<213> ORGANISM: Artificial Sequence
<220> FEATURE:
<223> OTHER INFORMATION: primer or probe

<400> SEQUENCE: 131
cttggtggca tggtttgtc                                                     19

<210> SEQ ID NO 132
<211> LENGTH: 20
<212> TYPE: DNA
<213> ORGANISM: Artificial Sequence
<220> FEATURE:
<223> OTHER INFORMATION: primer or probe

<400> SEQUENCE: 132
gctcagacac ccaaaagtcc                                                    20

<210> SEQ ID NO 133
<211> LENGTH: 24
<212> TYPE: DNA
<213> ORGANISM: Artificial Sequence
<220> FEATURE:
<223> OTHER INFORMATION: primer or probe

<400> SEQUENCE: 133
acgtgatgac tttgttggca tggc                                               24

<210> SEQ ID NO 134
<211> LENGTH: 25
<212> TYPE: DNA
<213> ORGANISM: Artificial Sequence
<220> FEATURE:
<223> OTHER INFORMATION: primer or probe

<400> SEQUENCE: 134
atcctgagta gtggtaatct actgg                                              25

<210> SEQ ID NO 135
<211> LENGTH: 40
<212> TYPE: DNA
<213> ORGANISM: Artificial Sequence
<220> FEATURE:
<223> OTHER INFORMATION: primer or probe

<400> SEQUENCE: 135
tcccgcgaaa ttaatacgac ttgcggagat tctcttcctc                              40

<210> SEQ ID NO 136
<211> LENGTH: 22
<212> TYPE: DNA
<213> ORGANISM: Artificial Sequence
<220> FEATURE:
<223> OTHER INFORMATION: primer or probe

<400> SEQUENCE: 136
tggtaatcta ctgggacgga ac                                                 22

<210> SEQ ID NO 137
<211> LENGTH: 88
<212> TYPE: DNA
<213> ORGANISM: Artificial Sequence
<220> FEATURE:
<223> OTHER INFORMATION: primer or probe

<400> SEQUENCE: 137
```

```
gtgtttgtgc ctgtcttcct tttacgacgg ctctgcctcc tgcctgcttc ttcgtgcctc    60
gttctcgtgt agactgggac ggaacagc                                       88
```

<210> SEQ ID NO 138
<211> LENGTH: 23
<212> TYPE: DNA
<213> ORGANISM: Artificial Sequence
<220> FEATURE:
<223> OTHER INFORMATION: primer or probe

<400> SEQUENCE: 138

```
gctttgaggt gcgtgtttgt gcc                                            23
```

<210> SEQ ID NO 139
<211> LENGTH: 20
<212> TYPE: DNA
<213> ORGANISM: Artificial Sequence
<220> FEATURE:
<223> OTHER INFORMATION: primer or probe

<400> SEQUENCE: 139

```
cccgaacagc tttgaggtgc                                                20
```

<210> SEQ ID NO 140
<211> LENGTH: 64
<212> TYPE: DNA
<213> ORGANISM: Artificial Sequence
<220> FEATURE:
<223> OTHER INFORMATION: primer or probe

<400> SEQUENCE: 140

```
cccgaacagc tttgaggtgc tcccgcgaaa ttaatacgac gccttagata aaactgagca    60
agag                                                                 64
```

<210> SEQ ID NO 141
<211> LENGTH: 21
<212> TYPE: DNA
<213> ORGANISM: Artificial Sequence
<220> FEATURE:
<223> OTHER INFORMATION: primer or probe

<400> SEQUENCE: 141

```
ggaagatcca atccattttt g                                              21
```

<210> SEQ ID NO 142
<211> LENGTH: 21
<212> TYPE: DNA
<213> ORGANISM: Artificial Sequence
<220> FEATURE:
<223> OTHER INFORMATION: primer or probe

<400> SEQUENCE: 142

```
caatccattt tgttgtcca g                                               21
```

<210> SEQ ID NO 143
<211> LENGTH: 91
<212> TYPE: DNA
<213> ORGANISM: Artificial Sequence
<220> FEATURE:
<223> OTHER INFORMATION: primer or probe

<400> SEQUENCE: 143

```
atttgtttca tgaaatactt cctttttacga cggctctgcc tcctgcctgc ttcttcgtgc    60
ctcgttctcg tgtagattgt tgtccagcca c                                   91
```

<210> SEQ ID NO 144
<211> LENGTH: 20
<212> TYPE: DNA
<213> ORGANISM: Artificial Sequence
<220> FEATURE:
<223> OTHER INFORMATION: primer or probe

<400> SEQUENCE: 144
ttgttgtcca gccaccatga                                              20

<210> SEQ ID NO 145
<211> LENGTH: 20
<212> TYPE: DNA
<213> ORGANISM: Artificial Sequence
<220> FEATURE:
<223> OTHER INFORMATION: primer or probe

<400> SEQUENCE: 145
ttgttgtcca gccaccatga                                              20

<210> SEQ ID NO 146
<211> LENGTH: 41
<212> TYPE: DNA
<213> ORGANISM: Artificial Sequence
<220> FEATURE:
<223> OTHER INFORMATION: primer or probe

<400> SEQUENCE: 146
tcccgcgaaa ttaatacgac tgacaaagaa cagctcaaag c                      41

<210> SEQ ID NO 147
<211> LENGTH: 24
<212> TYPE: DNA
<213> ORGANISM: Artificial Sequence
<220> FEATURE:
<223> OTHER INFORMATION: primer or probe

<400> SEQUENCE: 147
tccattttag cacttacctg tgac                                         24

<210> SEQ ID NO 148
<211> LENGTH: 25
<212> TYPE: DNA
<213> ORGANISM: Artificial Sequence
<220> FEATURE:
<223> OTHER INFORMATION: primer or probe

<400> SEQUENCE: 148
cttacctgtg actccataga aaatc                                        25

<210> SEQ ID NO 149
<211> LENGTH: 32
<212> TYPE: DNA
<213> ORGANISM: Artificial Sequence
<220> FEATURE:
<223> OTHER INFORMATION: primer or probe

<400> SEQUENCE: 149
cctgtgactc catagaaaat ctttctcctg ct                                32

<210> SEQ ID NO 150
<211> LENGTH: 47
<212> TYPE: DNA
<213> ORGANISM: Artificial Sequence
<220> FEATURE:

```
<223> OTHER INFORMATION: primer or probe

<400> SEQUENCE: 150
tcccgcgaaa ttaatacgac tgactgaata taaacttgtg gtagttg        47

<210> SEQ ID NO 151
<211> LENGTH: 23
<212> TYPE: DNA
<213> ORGANISM: Artificial Sequence
<220> FEATURE:
<223> OTHER INFORMATION: primer or probe

<400> SEQUENCE: 151
catattcgtc cacaaaatga ttc                                  23

<210> SEQ ID NO 152
<211> LENGTH: 26
<212> TYPE: DNA
<213> ORGANISM: Artificial Sequence
<220> FEATURE:
<223> OTHER INFORMATION: primer or probe

<400> SEQUENCE: 152
aatgattctg aattagctgt atcgtc                               26

<210> SEQ ID NO 153
<211> LENGTH: 115
<212> TYPE: DNA
<213> ORGANISM: Artificial Sequence
<220> FEATURE:
<223> OTHER INFORMATION: primer or probe

<400> SEQUENCE: 153
aatgattctg aattagctgt atcgtcgctc caactaccac attccttta cgacggctct    60 gcctcctgcc tgctcttcgt gctctcgttc tcgtgtagac ggcactcttg cctac        115

<210> SEQ ID NO 154
<211> LENGTH: 20
<212> TYPE: DNA
<213> ORGANISM: Artificial Sequence
<220> FEATURE:
<223> OTHER INFORMATION: primer or probe

<400> SEQUENCE: 154
ggcactcttg cctacgccac                                      20
```